(12) United States Patent
Gurfinkel et al.

(10) Patent No.: US 10,905,978 B2
(45) Date of Patent: Feb. 2, 2021

(54) METHOD AND APPARATUS FOR PROCESSING AND ANALYZING FILTERED PARTICLES

(71) Applicant: POCARED Diagnostics LTD., Rehovot (IL)

(72) Inventors: Jonathan Gurfinkel, Omer (IL); Gal Ingber, Oranit (IL)

(73) Assignee: POCARED Diagnostics LTD. (IL)

( * ) Notice: Subject to any disclaimer, the term of this patent is extended or adjusted under 35 U.S.C. 154(b) by 213 days.

(21) Appl. No.: 16/161,685

(22) Filed: Oct. 16, 2018

(65) Prior Publication Data

US 2019/0046902 A1 Feb. 14, 2019

Related U.S. Application Data

(62) Division of application No. 14/560,363, filed on Dec. 4, 2014, now Pat. No. 10,130,902.

(Continued)

(51) Int. Cl.
*B01D 29/00* (2006.01)
*G01N 1/30* (2006.01)
(Continued)

(52) U.S. Cl.
CPC ......... *B01D 29/0095* (2013.01); *B01D 37/00* (2013.01); *B01L 3/502753* (2013.01);
(Continued)

(58) Field of Classification Search
CPC ........ B01D 37/00; B01D 37/04; B01D 39/00; B01D 39/1692; B01D 39/14; B01D 39/16;
(Continued)

(56) References Cited

U.S. PATENT DOCUMENTS 3,754,868 A   8/1973   Witz et al.
3,770,349 A * 11/1973  Legorreta-Sanchez ..................... G06M 1/101
                                                                    356/73

(Continued)

FOREIGN PATENT DOCUMENTS

EP     1179585 A2   12/1998
EP     2645078 A1   10/2013

(Continued)

OTHER PUBLICATIONS

Weinbauer et al. Utility of Green Fluorescent Nucleic Acid Dyes and Aluminum Oxide Membrane Filters for Rapid Epifluorescence Enumeration of Soil and Sediment Bacteria. Applied and Environmental Microbiology, Dec. 1998, vol. 64, No. 12, p. 5000-5003. (Year: 1998).*

(Continued)

*Primary Examiner* — Katherine Zalasky McDonald
(74) *Attorney, Agent, or Firm* — The Webb Law Firm

(57) ABSTRACT

A filter arrangement with a top element and a bottom element and a filter element therebetween captures oversized particles on the upper surface of the filter element and tangentially rinses these particles using an elution fluid to provide a concentration of particles in a relatively low volume of fluid for further analysis. A configuration using a slider valve may also be utilized. Additionally, an arrangement of supply and receiving containers may be used to minimize the number of containers required. A mass flow meter may be incorporated to measure the flow of elution fluid. Finally, a wash stage of the filtering process may be used to introduce stain onto the particles for further analysis, such as that associated with Gram staining and these stained particles may be further analyzed.

10 Claims, 41 Drawing Sheets

Related U.S. Application Data

(60) Provisional application No. 61/911,840, filed on Dec. 4, 2013, provisional application No. 62/017,604, filed on Jun. 26, 2014, provisional application No. 62/050,859, filed on Sep. 16, 2014.

(51) Int. Cl.

| | |
|---|---|
| B01D 37/00 | (2006.01) |
| G01N 1/40 | (2006.01) |
| G01N 1/28 | (2006.01) |
| G01G 17/06 | (2006.01) |
| B01L 3/00 | (2006.01) |
| G01N 33/493 | (2006.01) |
| C12Q 1/24 | (2006.01) |
| G01N 5/02 | (2006.01) |
| G01N 15/00 | (2006.01) |
| G01F 15/12 | (2006.01) |

(52) U.S. Cl.
CPC .............. *C12Q 1/24* (2013.01); *G01G 17/06* (2013.01); *G01N 1/30* (2013.01); *G01N 1/4077* (2013.01); *G01N 33/493* (2013.01); *B01L 2300/0681* (2013.01); *B01L 2400/0487* (2013.01); *B01L 2400/065* (2013.01); *B01L 2400/0622* (2013.01); *G01F 15/125* (2013.01); *G01N 1/2813* (2013.01); *G01N 5/02* (2013.01); *G01N 2001/302* (2013.01); *G01N 2001/4088* (2013.01); *G01N 2015/0053* (2013.01); *Y10T 436/25375* (2015.01)

(58) Field of Classification Search
CPC ...... B01D 35/00; B01D 35/30; B01D 35/301; B01D 35/303; B01D 2201/18; B01D 2201/184; B01D 2221/10; B01D 2239/12; B01D 2239/1216; B01D 2257/91; B01D 29/01; G01N 1/30; G01N 1/40; G01N 1/4005; G01N 2001/4016; G01N 2001/4088; G01N 2001/302
See application file for complete search history.

(56) References Cited

U.S. PATENT DOCUMENTS

| | | | |
|---|---|---|---|
| 4,096,062 A | 6/1978 | Myreen et al. | |
| 4,427,415 A | 1/1984 | Cleveland | |
| 5,180,606 A | 1/1993 | Stokes et al. | |
| 5,375,477 A | 12/1994 | Neill | |
| 5,380,437 A | 1/1995 | Bertoncini | |
| 5,603,900 A | 2/1997 | Clark | |
| 5,683,658 A | 11/1997 | Reischl et al. | |
| 5,947,689 A | 9/1999 | Schick | |
| 5,976,824 A | 11/1999 | Gordon | |
| 6,338,802 B1 | 1/2002 | Bodner et al. | |
| 6,692,702 B1 | 2/2004 | Burshteyn et al. | |
| 7,100,461 B2 | 9/2006 | Bradley et al. | |
| 7,166,443 B2* | 1/2007 | Walker .............. B01L 3/502761 | |
| | | | 435/34 |
| 7,240,572 B2 | 7/2007 | Pitt et al. | |
| 7,374,724 B2 | 5/2008 | Ingenhoven et al. | |
| 7,510,654 B2 | 3/2009 | Mir et al. | |
| 7,682,511 B2 | 3/2010 | de los Reyes et al. | |
| 7,695,627 B2 | 4/2010 | Bosch et al. | |
| 8,007,743 B2 | 8/2011 | Clark et al. | |
| 8,033,187 B2 | 10/2011 | Sann et al. | |
| 8,110,112 B2 | 2/2012 | Alburty et al. | |
| 8,584,535 B2 | 11/2013 | Page et al. | |
| 8,584,536 B2 | 11/2013 | Page et al. | |
| 2002/0030015 A1 | 3/2002 | Stipanovic et al. | |
| 2004/0026322 A1 | 2/2004 | Nussbaumer et al. | |
| 2004/0132198 A1 | 7/2004 | Burshteyn et al. | |
| 2004/0132208 A1 | 7/2004 | Burshteyn et al. | |
| 2005/0173315 A1 | 8/2005 | Bosch et al. | |
| 2005/0194316 A1* | 9/2005 | Pourahmadi .......... C12M 47/06 | |
| | | | 210/638 |
| 2006/0254972 A1* | 11/2006 | Tai ........................ B01D 71/022 | |
| | | | 210/321.6 |
| 2007/0025883 A1* | 2/2007 | Tai ...................... B01D 67/0034 | |
| | | | 422/400 |
| 2008/0023381 A1 | 1/2008 | Jackson et al. | |
| 2008/0237142 A1 | 10/2008 | Carpenter et al. | |
| 2009/0126514 A1 | 5/2009 | Burroughs et al. | |
| 2009/0217777 A1 | 9/2009 | Hanson et al. | |
| 2009/0277833 A1 | 11/2009 | Mir et al. | |
| 2009/0280565 A1 | 11/2009 | Jolicoeur et al. | |
| 2010/0051527 A1 | 3/2010 | Frandsen | |
| 2010/0068706 A1 | 3/2010 | Pourahmadi et al. | |
| 2010/0313685 A1 | 12/2010 | Page et al. | |
| 2010/0313686 A1 | 12/2010 | Page et al. | |
| 2011/0053152 A1* | 3/2011 | Goldkorn ............. C12Q 1/6886 | |
| | | | 435/6.14 |
| 2011/0061474 A1 | 3/2011 | Page et al. | |
| 2011/0108483 A1 | 5/2011 | Kaas | |
| 2011/0197685 A1 | 8/2011 | Alburty et al. | |
| 2012/0156716 A1 | 6/2012 | Walsh et al. | |
| 2012/0322792 A1* | 12/2012 | Narla .................... A61K 31/517 | |
| | | | 514/217 |
| 2013/0045496 A1 | 2/2013 | Jansen | |
| 2013/0045532 A1 | 2/2013 | Hyman et al. | |
| 2013/0059326 A1 | 3/2013 | Waiche et al. | |
| 2013/0086980 A1 | 4/2013 | Gadini et al. | |
| 2013/0315780 A1 | 11/2013 | Cook | |
| 2013/0337432 A1* | 12/2013 | Cook ........................ B65B 1/04 | |
| | | | 435/2 |
| 2014/0246389 A1 | 9/2014 | Ingber | |

FOREIGN PATENT DOCUMENTS

| | | |
|---|---|---|
| JP | S6138948 A | 2/1986 |
| JP | S63202741 A | 8/1988 |
| JP | 200195557 A | 4/2001 |
| JP | 2004329033 A | 11/2004 |
| JP | 2009136169 A | 6/2009 |
| JP | 3155072 U | 10/2009 |
| JP | 201054335 A | 3/2010 |
| WO | 2008151093 A1 | 12/2008 |
| WO | 2012086763 A1 | 6/2012 |
| WO | 2013173524 A2 | 11/2013 |
| WO | 2014123896 A1 | 11/2013 |

OTHER PUBLICATIONS

Romero et al. Rapid Method for the Differentiation of Gram-Positive and Gram-Negative Bacteria on Membrane Filters. Journal of Clinical Microbiology, July 1988, vol. 26, No. 7, p. 1378-1382. (Year: 1988).*

Molecular Probes. LIVE BacLight™ Bacterial Gram Stain Kit (L-7005) Product Information, Feb. 8, 2011, 6 pages. (Year: 2011).*

Juniper et al. A Filter Membrane Technique for Cytological Study of Exfoliated Cells in Body Fluids. Cancer Mar.-Apr. 1959, vol. 12, 278-285. (Year: 1959).*

Elliott, D. C., and T. Y. Barila. 1987. Membrane filtration—fluorescent antibody staining prcocedure for detecting and quantifying Renibacterium salmoninarum in coelomic fluid of chinook salmon (*Oncorhynchus tshawytscha*). Can. J. Fish. Aquat. Sci. 44: 206-210. (Year: 1987).*

Japanese Office Action 2016-536719 dated Nov. 30, 2013.

Bourbeau et al, "First Evaluation of the WASP, a New Automated Microbiology Plating Instrument", J. Clin. Microbiol. Apr. 2009, p. 1101-1106, vol. 47, No. 4.

Copan Diagnostic, Inc., "WASP™ Walk Away Specimen Processor".

Copan Diagnostic, Inc., "WASP®: General Information".

Kim et al., "A rapid and economic in-house DNA purification method using glass syringe filters", PLoS ONE 4(11 ):e7750 (2009) p. 1-7.

(56) References Cited

OTHER PUBLICATIONS

NIH, "What goes in chemical waste containers," available at <https://www.orf.od.nih.gov/EnvironmentalProtection/WasteDisposal/Pages/WhatGoesinChemicalWasteContainers.aspx>, last updated Dec. 14, 2012, accessed Sep. 12, 2017, p. 1-2.
Tanny et al., "Improved filtration technique for concentrating and harvesting bacteria," Applied and Environmental Microbiology, Aug. 1980 ,p. 269-273.
Zierdt, "Adherence of bacteria, yeast, blood cells, and latex spheres to large-porosity membrane filters," Applied and Environmental Microbiology, Dec. 1979, p. 1166-1172.

* cited by examiner

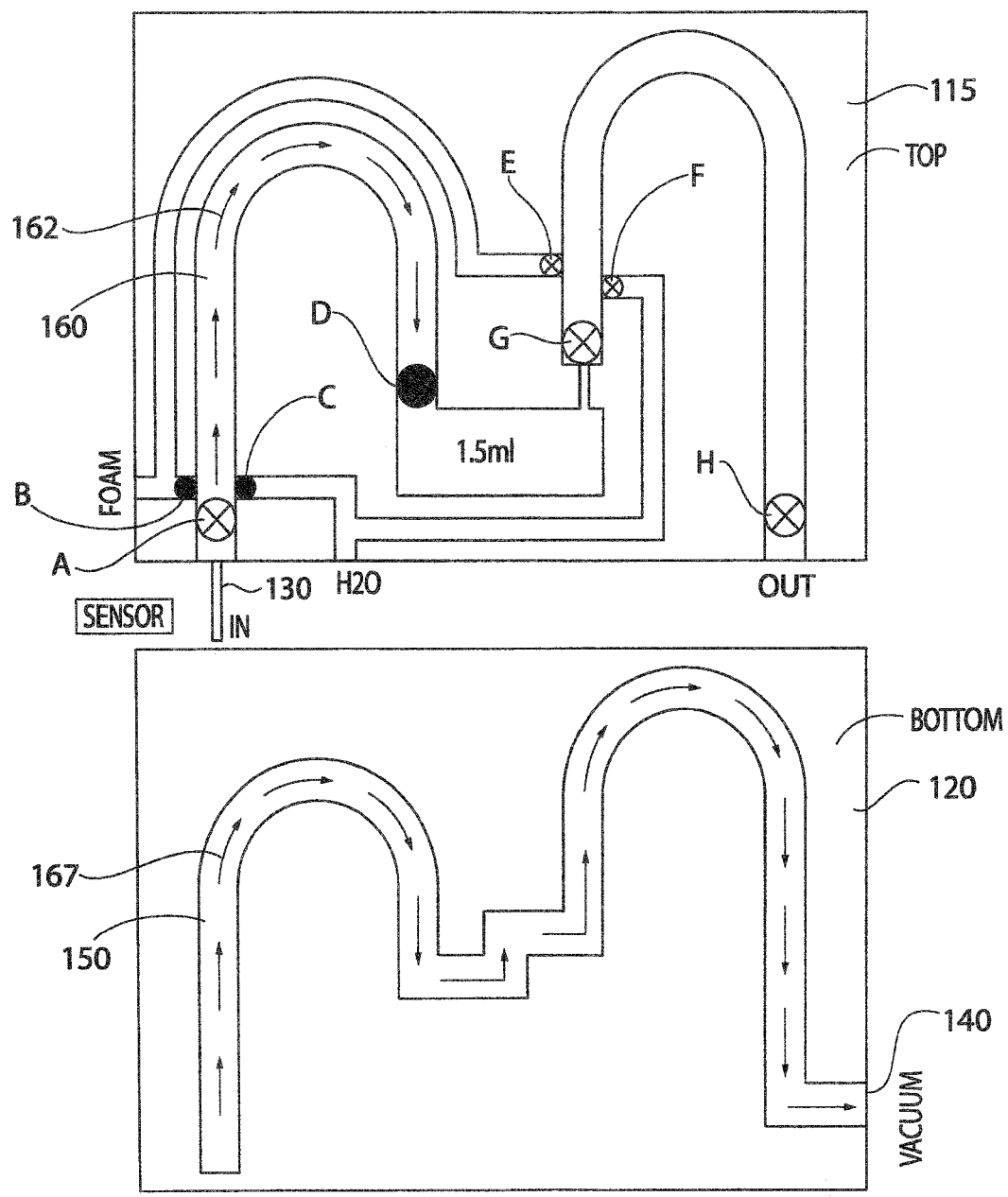
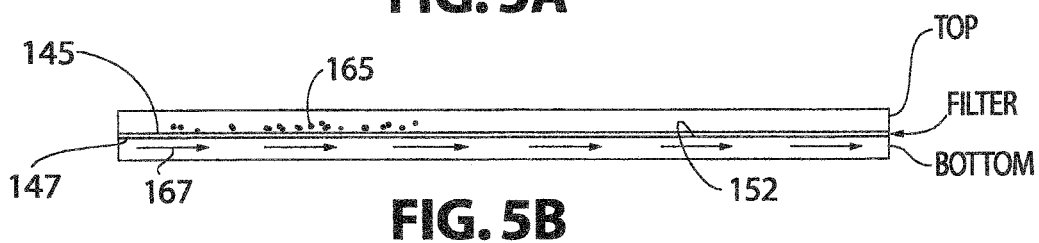
FIG. 5A
FIG. 5B

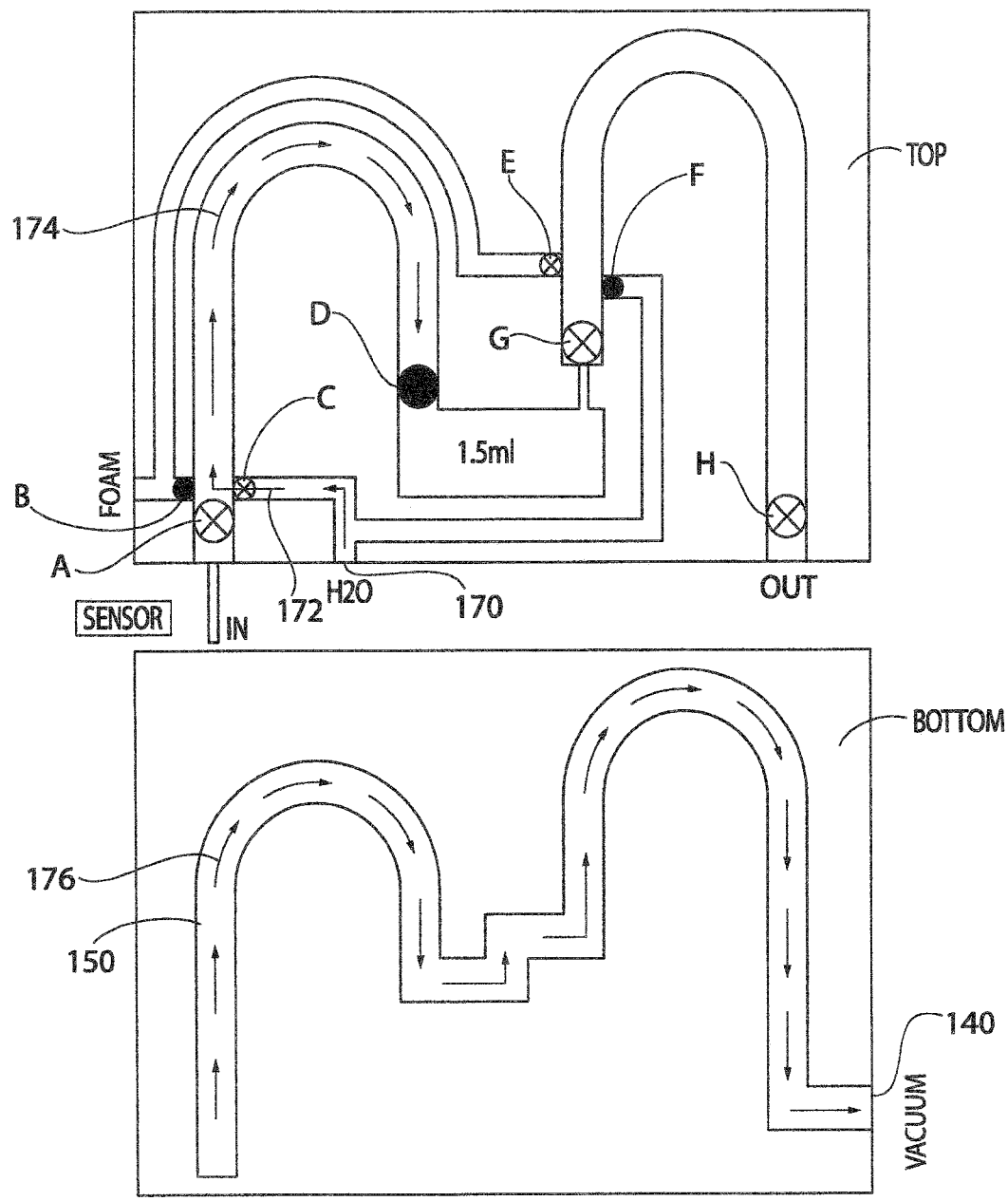
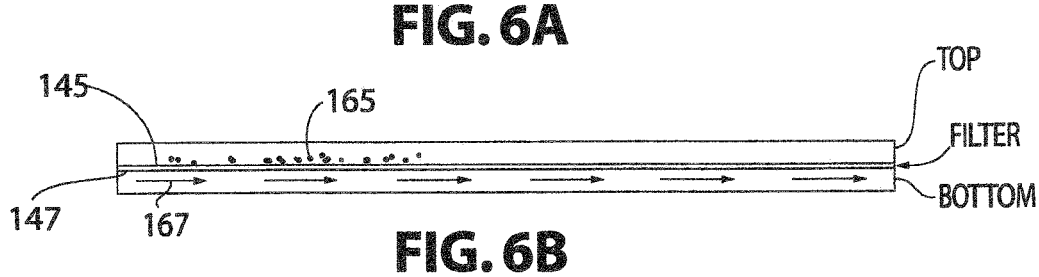
FIG. 6A
FIG. 6B

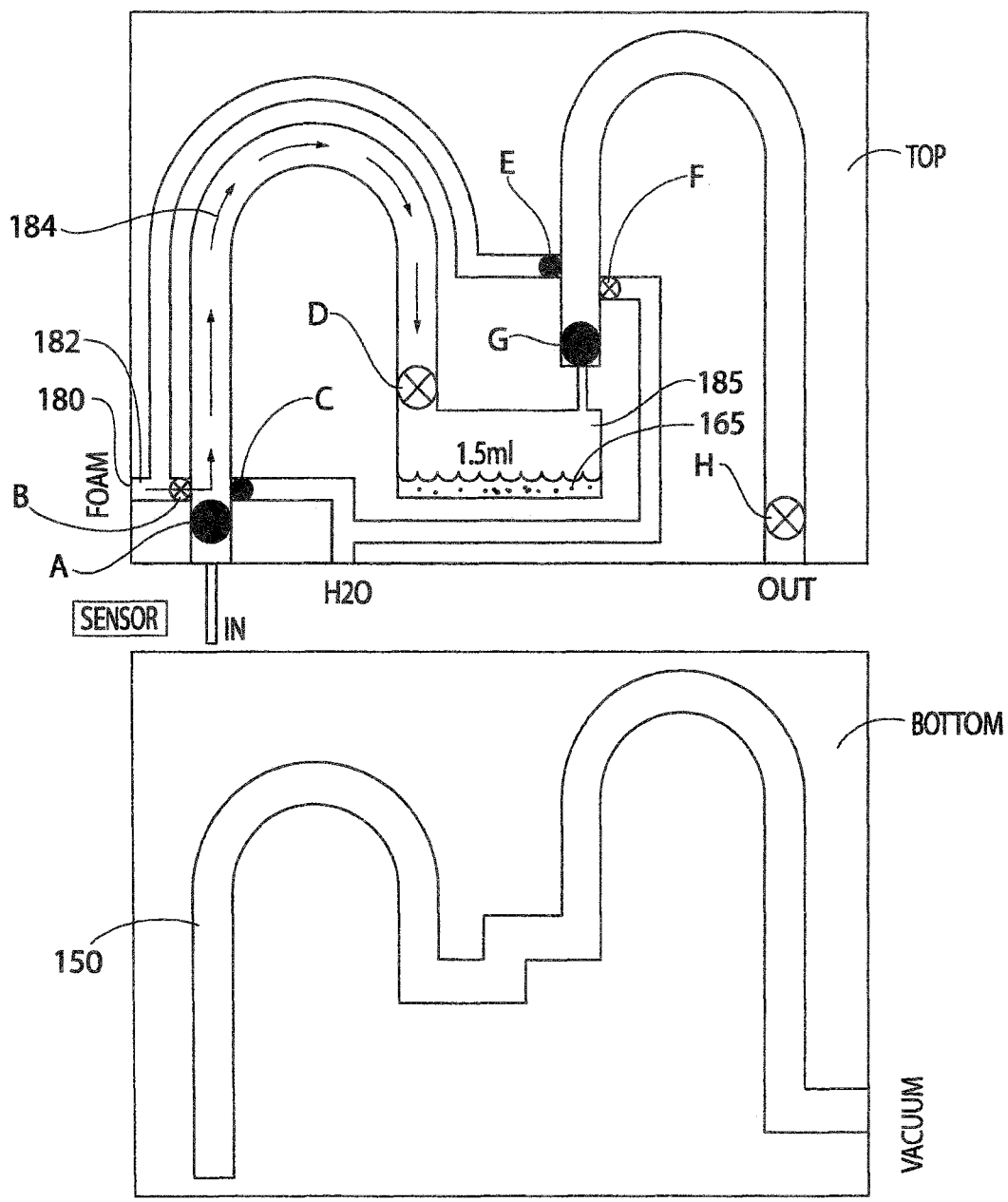
FIG. 7A
FIG. 7B

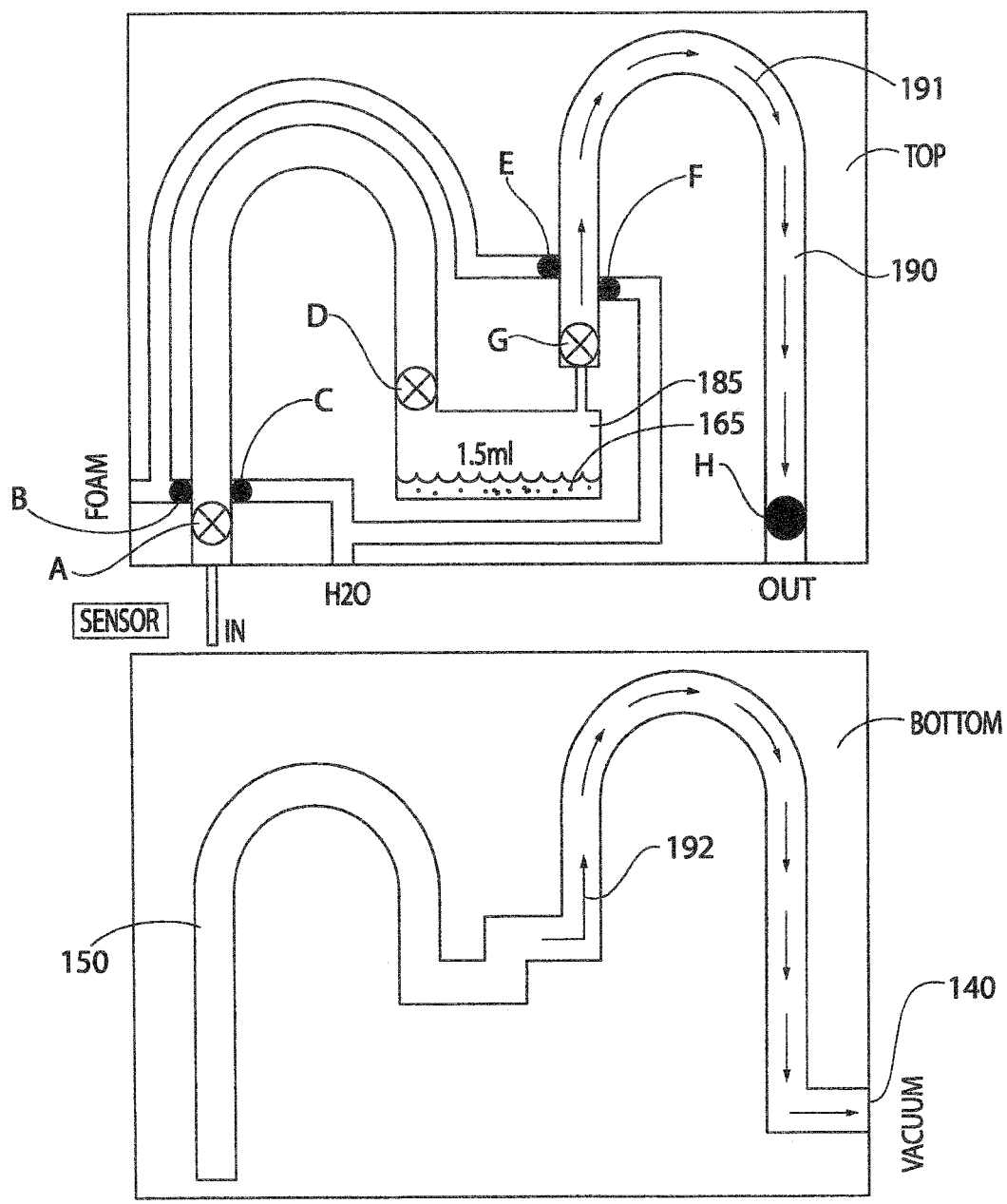
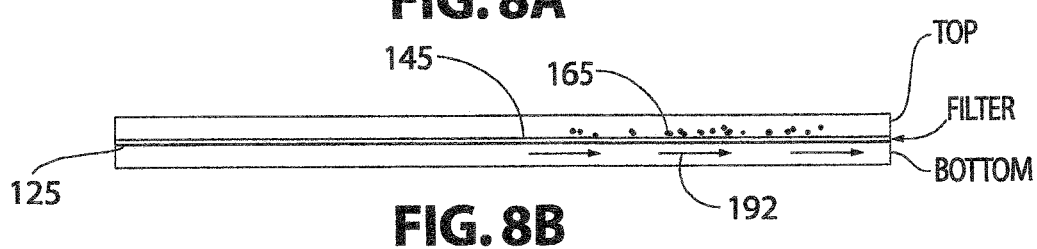
FIG. 8A
FIG. 8B

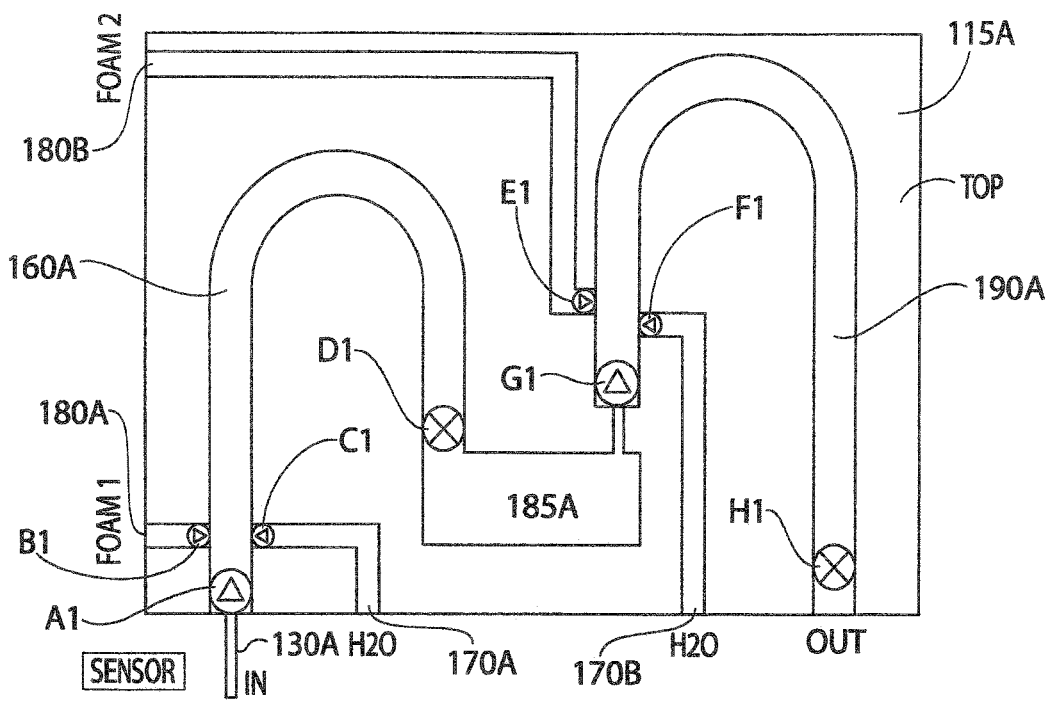
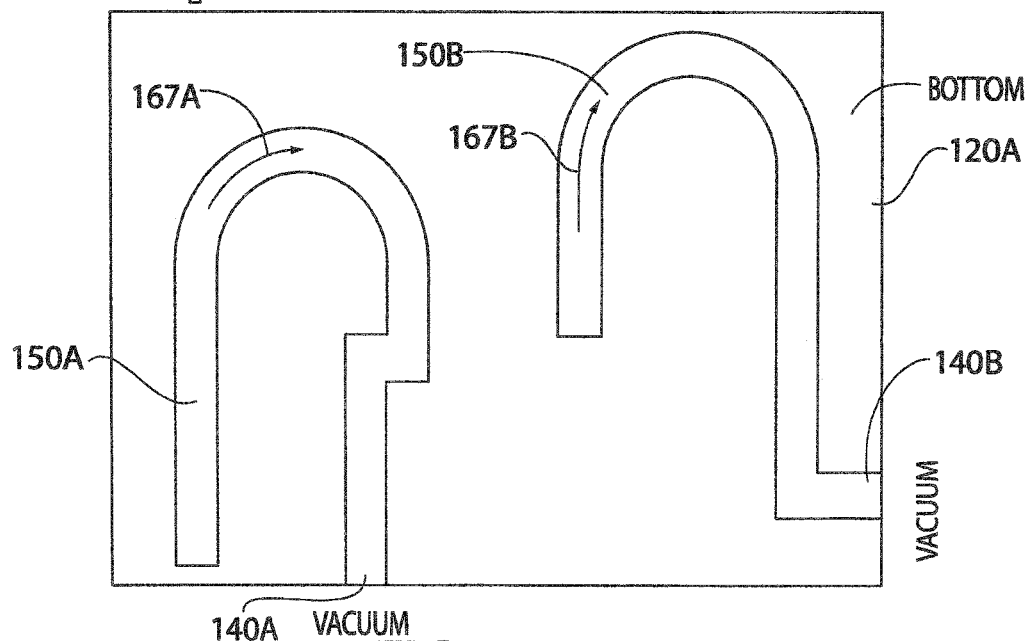
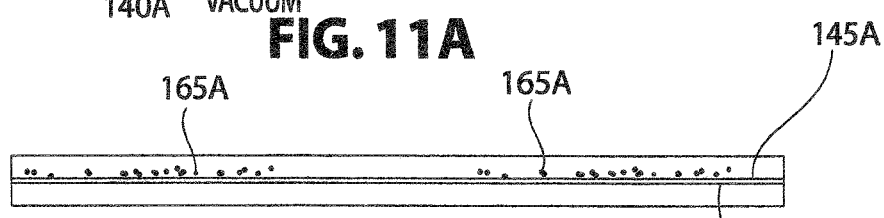
FIG. 11A
FIG. 11B

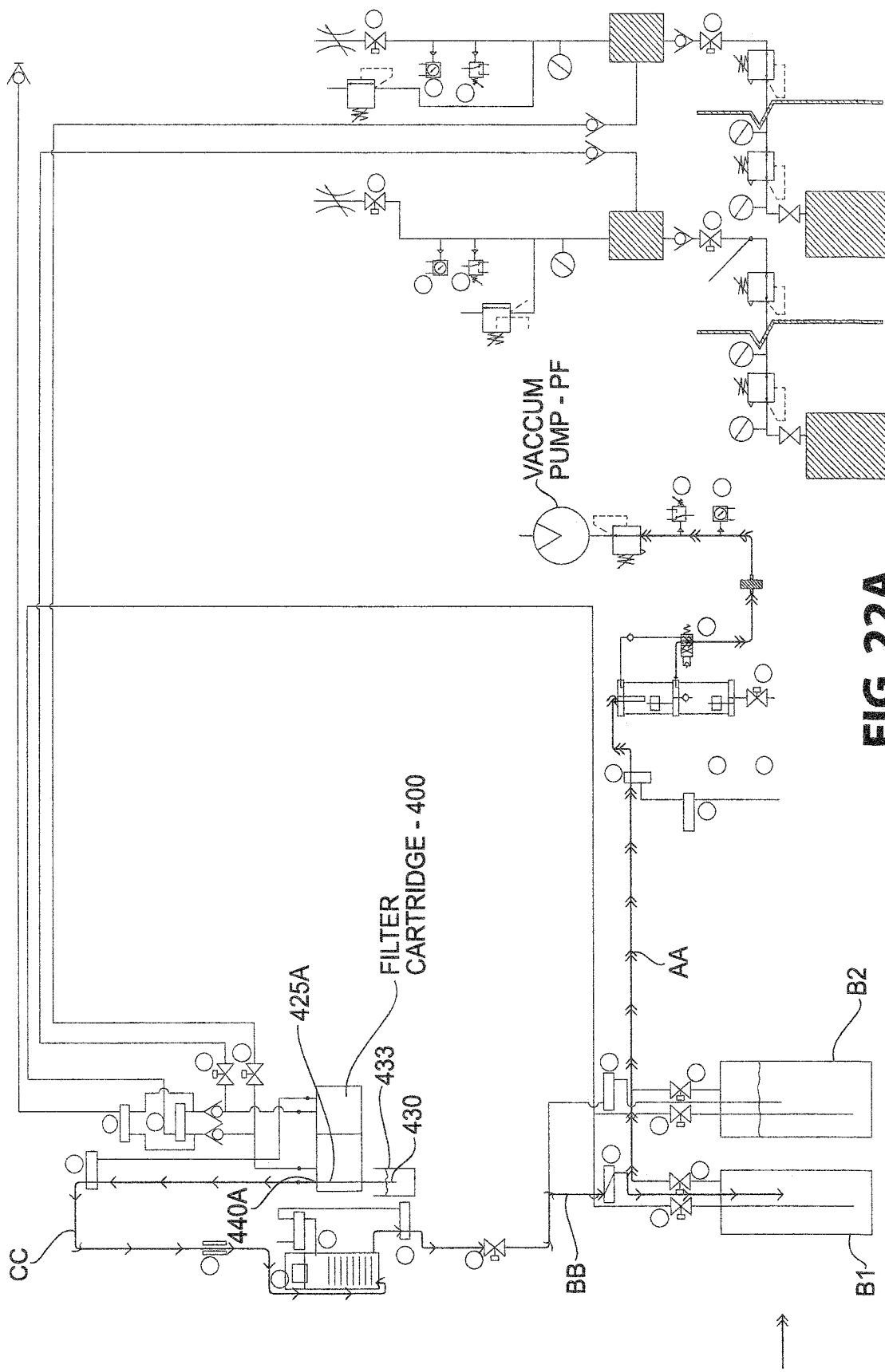

1 μl of Clinical Urine
specimen plated on
Blood agar using the
WASP

μl of Clinical Urine
pecimen plated on
hromagar using the
VASP

10 μl of Clinical Urine specimen placed on the slide.
Before: Proteins, cells and junk. Candida was not detected.
After: Candida cells are seen.

Same sample, 2 different oil immersion fields on the slide

10 µl of CU specimen placed on the slide.
Before: Proteins and junk. No cells were detected.
After: Epithelial cells are seen. Cells are intact.

METHOD AND APPARATUS FOR PROCESSING AND ANALYZING FILTERED PARTICLES

CROSS-REFERENCE TO RELATED APPLICATIONS

This application is a divisional of U.S. patent application Ser. No. 14/560,363 filed Dec. 4, 2014, which claims the benefit of U.S. Provisional Application No. 61/911,840, filed Dec. 4, 2013, U.S. Provisional Application No. 62/017,604 filed Jun. 26, 2014, and U.S. Provisional Application No. 62/050,859 filed Sep. 16, 2014. The disclosure of each of these documents is hereby incorporated in its entirety by reference.

BACKGROUND OF THE INVENTION

Field of the Invention

Mechanical particle filters are used to extract particles for analysis from a fluid/particle mixture. However, now the particles are retained by the filter. The most common technique for removing particles from a filter for analysis is to introduce additional fluid, such as by using a backwashing process. However, ideally, the particles should be contained in the smallest amount of fluid possible while maintaining high retention ratio for ease of analysis. This is especially true when the particles are bacteria. Therefore, while backwashing a filter does remove the particles from the filter, the efficiency of the process is low and the quantity of fluid required may produce a secondary fluid/particle mixture with excessive fluid.

Furthermore, when using hydrophilic membrane with small pore size and when suction is provided on the downstream side of the filter to draw fluid and undersized particles, often times, the membrane will become a barrier to air after it was wetted.

A design and method are needed, whereby the particles of interest may be filtered and contained within a small volume of fluid and, furthermore, whereby the filter may be constructed such that, even after the fluid passes, the membranes of the filter will allow more suction using vacuum.

BRIEF DESCRIPTION OF THE DRAWINGS

FIGS. 5A-10A are schematic views of the top half and bottom half of one embodiment of the filter arrangement in accordance with the subject invention illustrating different configurations for the filtering process;

FIGS. 5B-10B are schematics of the filter arrangement in the assembled state showing different configurations for the filtering process;

FIG. 11A is a schematic view of the top half and bottom half of one embodiment of the filter arrangement utilizing check valves and modified channels to provide dual inlets for the elution and water and dual outlets for the vacuum;

FIG. 11B is a schematic view of the filter arrangement in FIG. 11A in the assembled state;

FIGS. 12A-17A are schematic views of the top half and bottom half of another embodiment of the filter arrangement illustrating different configurations for the filtering process and, furthermore, utilizing stopcock valves to create different fluid paths;

FIGS. 12B-17B are schematic views of the filter arrangement of the embodiment illustrated in FIGS. 12A-17A in the assembled state showing different configurations for the filtering process;

FIGS. 22A, 23A, 25A, 26A, and 28A are process flow diagrams showing the system in which the filter arrangements, also referred to as filter cartridges, are utilized for the cartridge configurations shown in FIGS. 22-28;

DESCRIPTION OF THE INVENTION

Figure 1:
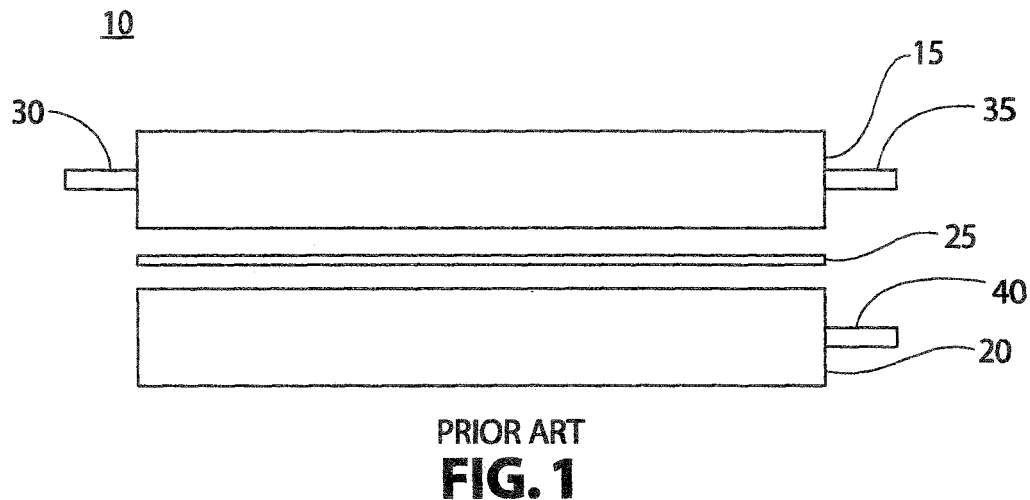
FIG. 1 is an exploded view of a simplified schematic showing a prior art filter arrangement.

For purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
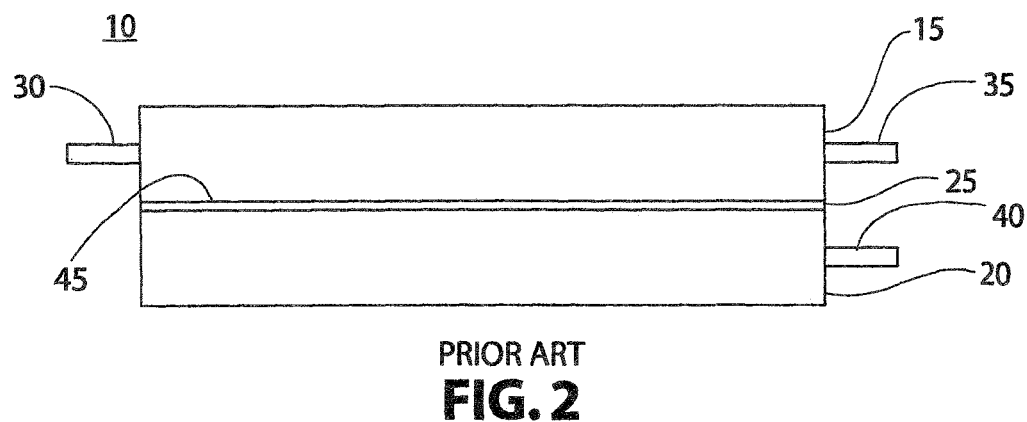
FIG. 2 is an assembled view of a schematic of the filter arrangement in FIG. 1.

FIG. 1 illustrates a prior art filter arrangement 10 having a top element 15, a bottom element 20, and a filter element 25 therebetween. FIG. 1 is an exploded schematic view, while FIG. 2 is an assembled schematic view of the same parts but with the top element 15 and the bottom element 20 drawn together to compress the filter element 25 therebetween. As an overview, directing attention to FIG. 2, a fluid/particle mixture is introduced through inlet/outlet 30 into channels (not shown) extending through the top element 15. Inlet 35 is closed and a suction outlet 40 provides a vacuum drawing the fluid/particle mixture through the filter element 25, such that oversized particles remain on the upper surface 45 of the filter element 25. Thereafter, the inlet 35 is open and the suction outlet 40 is closed. An elution fluid is then introduced into the inlet 35 to tangentially rinse the upper surface 45 of the filter element 25. This provides a reduced volume fluid/particle mixture that exits the inlet/outlet 30. As an intermediate step, it is possible to close the inlet 35 and to introduce a water/rinse into the inlet/outlet 30, while suction outlet 40 is open, to wash over the particles after the initial filtering step to further filter any remaining particles that were not previously washed through the filter. This water/rinse and undersized particle solution are removed through the suction outlet 40 and discarded. As a result, the oversized particles that were deposited upon the upper surface 45 of the filter element 25 are isolated and collected using a reduced volume elution fluid.

Figure 3:
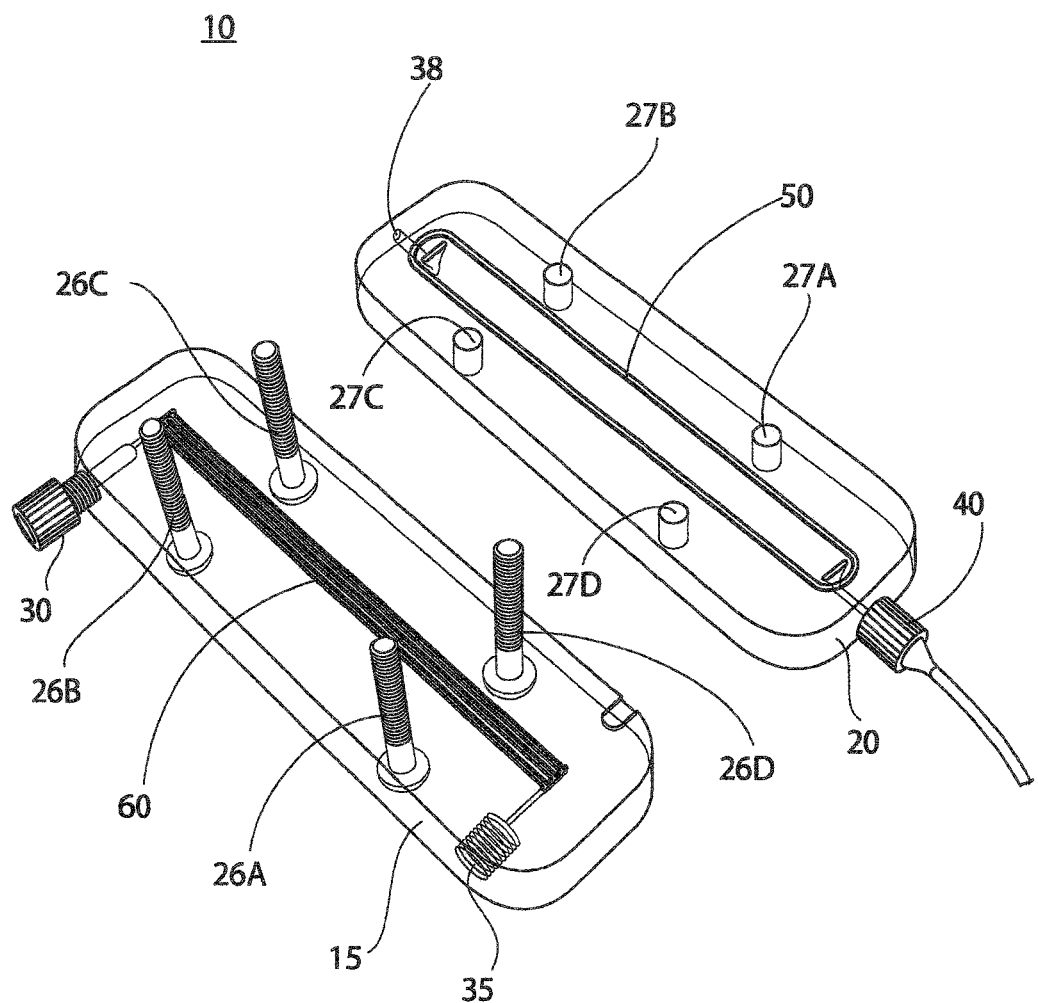
FIG. 3 is a schematic illustrating a perspective arrangement of a prior art the filter arrangement disassembled and without the filter element.
Figure 4:
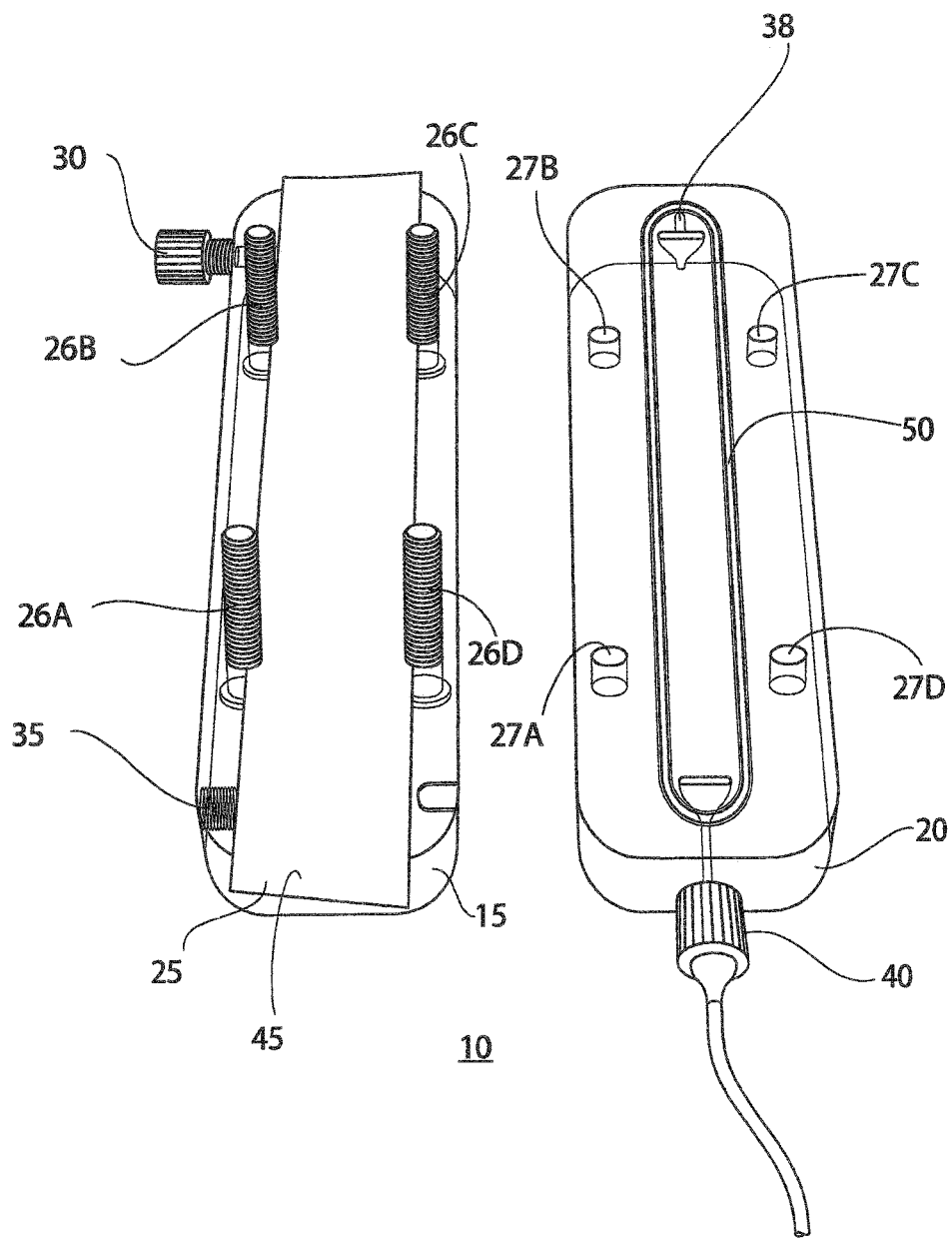
FIG. 4 is a schematic of the embodiment of the prior art filter arrangement of FIG. 3 but with a filter element placed in position.

FIGS. 3 and 4 illustrate a prior art embodiment of the filter arrangement 10 having a top element 20 and a bottom element 15 with a filter element 25 (FIG. 4) therebetween. Each of these figures is illustrated with a filter arrangement 10 in a disassembled state. However, it can be appreciated that the four bolts 26a, 26b, 26c, 26d may be secured within the bores 27a, 27b, 27c, 27d, respectively, with the filter element 25 therebetween to assemble the filter arrangement 10. The filter arrangement 10 illustrated in FIGS. 3 and 4, is a single-stage filter and the suction outlet 35 provides suction to the bottom channel 60. The top element 20 has an inlet/outlet 40 and an inlet 38, on the opposite side of inlet/outlet 40, with a channel 50 therebetween. The filter element 25 is positioned between the top element 20 and the bottom element 15. In operation, suction is provided at the suction outlet 35 such that there is a vacuum created in the bottom channel 60. The fluid/particle mixture is introduced through the inlet/outlet 40 of the top element 20 where it travels over the filter element 25 and oversized particles are retained on the upper surface 45 of the filter element 25. The fluid and undersized particles travel through the filter element 25 into the bottom channel 60 and are removed through the suction outlet 40. The oversized particles remain on the upper surface 45 of the filter element 25. Thereafter, suction is discontinued and elution fluid, under pressure, is introduced through the inlet 38 and into the channel 50 where it traverses the upper surface 45 and flushes the oversized particles into the outlet 40 where they are retained in a collector (not shown) for further analysis. The arrangement illustrated in FIGS. 3 and 4 does not include the intermediate step of rinsing the particles retained on the filter element 25 with water.

As known in the prior art, the elution fluid may be effervescent and contain a foaming agent such as TWEEN The subject filtering arrangement is most effective when the particles are bacteria. The filter element is preferably a polycarbonate-type filter which is a surface filter and may have pores with openings between approximately 0.01 and 50 microns. In one embodiment the openings are preferably approximately 0.4 microns wide.

For purposes of discussion, similar elements in different embodiments will be identified with similar numbers but with increments of 100, such as 10, 110, 210.

During the discussion of FIGS. 5A-10A, it should be appreciated that the surfaces illustrated for the top element 115 and the bottom element 120 may be transparent and the top element 115 will be placed over the bottom element 120, such that the channels in each of these elements 115, 120 are generally aligned with one another. Therefore, for purposes of discussion, the top element 115 is transparent and the channels illustrated therein will be on the underside 147 (FIG. 5B) of the top element 115, while the bottom channel 150 illustrated in the bottom element 120 is on the upper surface 152 of the bottom element 120. The filter element 25 is not illustrated in FIGS. 5A-10A but is located between the top portion element 115 and the bottom element 120 as shown in FIGS. 5B-10B.

Valves A-H are illustrated in the top element 115. Depending upon the configuration of the filter arrangement 110, one or more of these valves will be open and others will be closed. Such closing will be illustrated by darkening the valve symbol.

For the initial configuration, directing attention to FIGS. 5A and 5B, the fluid/particle mixture is introduced through the inlet 130 and travels through the first-stage channel 160 as indicated by arrow 162. Valve A is open while valves B, C, and D are closed. In this configuration, a vacuum will be activated such that the suction outlet 140 draws a vacuum through the entire bottom channel 150. As a result, the fluid/particle mixture is urged against the upper surface 145 of the filter element 125 (FIG. 5B), thereby retaining oversized particles 165 on the upper surface 145 of the filter element 125. Undersized particles, along with fluid, are drawn through the filter element 125 and evacuated along the bottom channel 150 through the suction outlet 140, as indicated by arrows 67. At this point, oversized particles 165 and other miscellaneous particles have been deposited upon the upper surface 145 of the filter element 125. It should be noted that for the arrangement illustrated in FIGS. 5A and 5B, no more than one-half of the filter element 125 has been utilized.

To improve the integrity of the filtering process, the Inventors have learned that additional undersized particles will be washed through the filter element 125 simply by providing a fluid rinse, such as a water rinse, over the particles 165.

Directing attention to FIGS. 6A and 6B, valves A, B, D, and F are closed and water is introduced through water inlet 170 along the water channel 172, as illustrated by arrows 174. Just as with the original fluid/particle mixture, the suction outlet 140 provides a vacuum to the bottom channel 150 such that the water is drawn through the filter element 125 into the bottom channel 150 and follows arrows 176 where it is discharged at the suction outlet 140. This water rinse removes additional undersized particles that may have been retained during the initial filter step.

Direction attention to FIGS. 7A and 7B, valves A, C, E, and G are now closed and the elution fluid, which will also be referred to as foam, is introduced under pressure at the foam inlet 180 where it travels through the foam channel 182 in a path defined by arrows 184 to a collector 185, which now contains a reduced volume fluid/particle mixture, wherein the fluid is the elution fluid. It should be noted that the vacuum is off, such that the bottom channel 150 is inactive and the flow of the elution fluid travels across the upper surface 145 of the filter element 125 to deposit the fluid/particle mixture within the collector 185. This process of passing the fluid across the upper surface 145 of the filter element 125 is known as tangentially rinsing the upper surface 152 and dislodges the particles on the upper surface 145 to mechanically scrape the upper surface 145 and move the particles 165 into the collector 185. By doing so, the relatively large volume of fluid associated with the initial fluid/particle mixture has been significantly reduced.

What has been described so far is a single-stage filtering process that provides a significant reduction in the volume of fluid associated with filtered particles to improve the ease of subsequent examination of the particles. Only a portion of the filter element 125, which extends essentially across the width of the bottom element 120, has been utilized.

The Inventors have realized that it is possible to provide a dual-stage filter with relative ease to further reduce the volume of fluid in the fluid/particle mixture or to further remove undesired small particles.

Directing attention to FIGS. 8A and 8B, with the refined fluid particle sample in the collector 185, valves B, C, E, F, and H are closed and suction is introduced to the bottom channel 150 such that fluid from the collector 185 is drawn into the second-stage channel 190 along arrows 191, where the undersized particles and the fluid are drawn through the filter element 125 into the bottom channel 150 and discharged through the suction outlet 140 along arrows 192. Additionally, valves A and D are open so that air can come in to permit fluid to be pulled out of reservoir 85. Once again, particles 165 are deposited upon the upper surface 145 of the filter element 125 but now the elution fluid and undersized particles are passed through the filter element 125 into the bottom channel 150 and out the suction outlet 140.

Figure 9A:
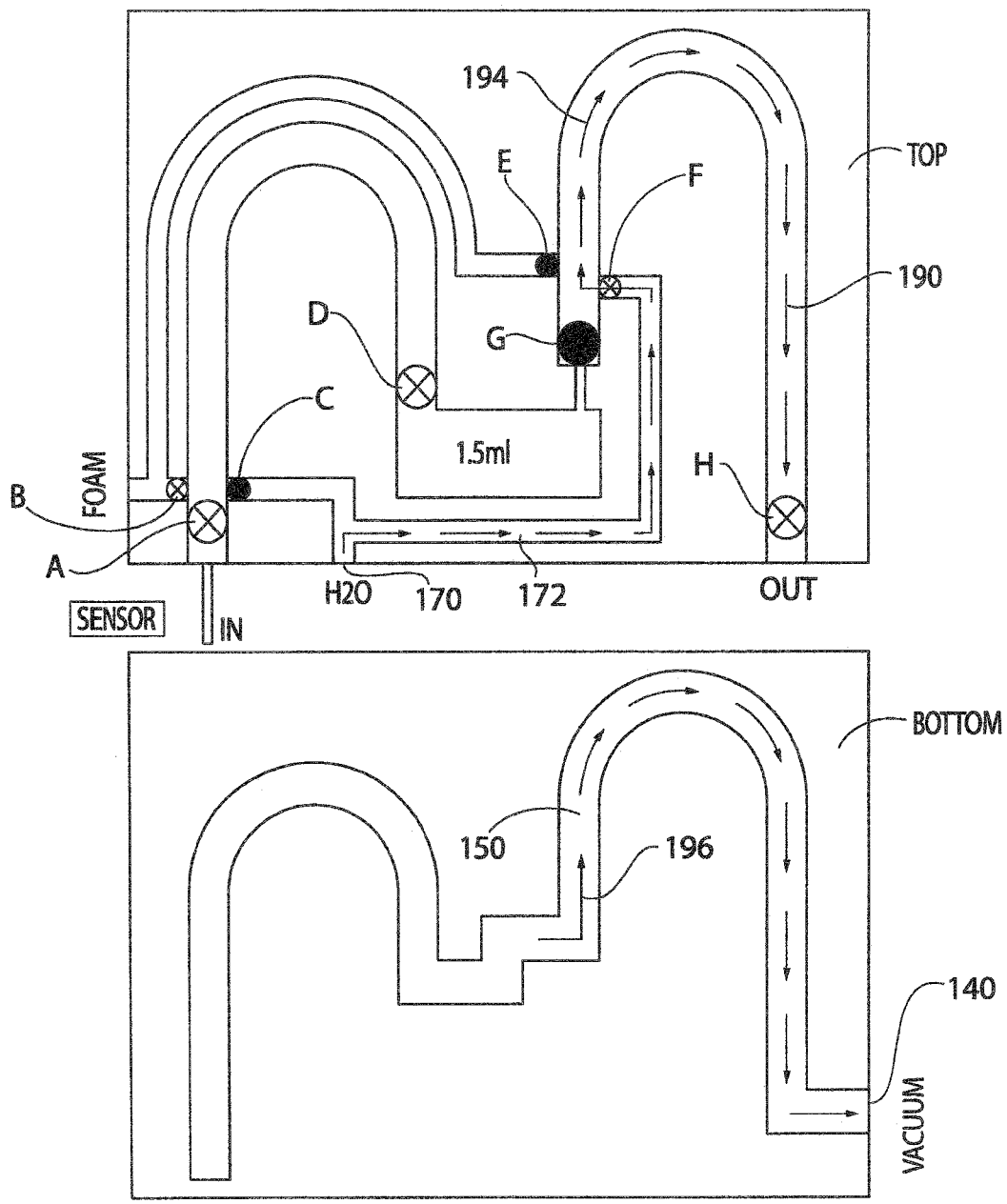
Figure 9B:
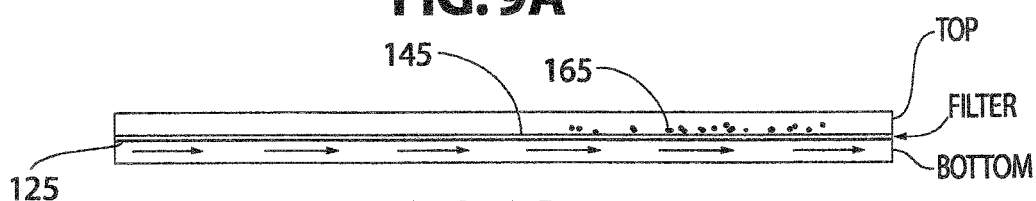

Directing attention to FIGS. 9A and 9B, valves C, E, G, and H are closed and water is introduced into the water channel 172 through the water inlet 170 and then into the second-stage channel 190 along arrows 194. With suction provided in the bottom channel 150, any undersized particles and the elution fluid remains are again drawn through the filter 125 into the bottom channel 150 where they follow the flow of arrows 196 and are discharged through the suction outlet 140.

Figure 10A:
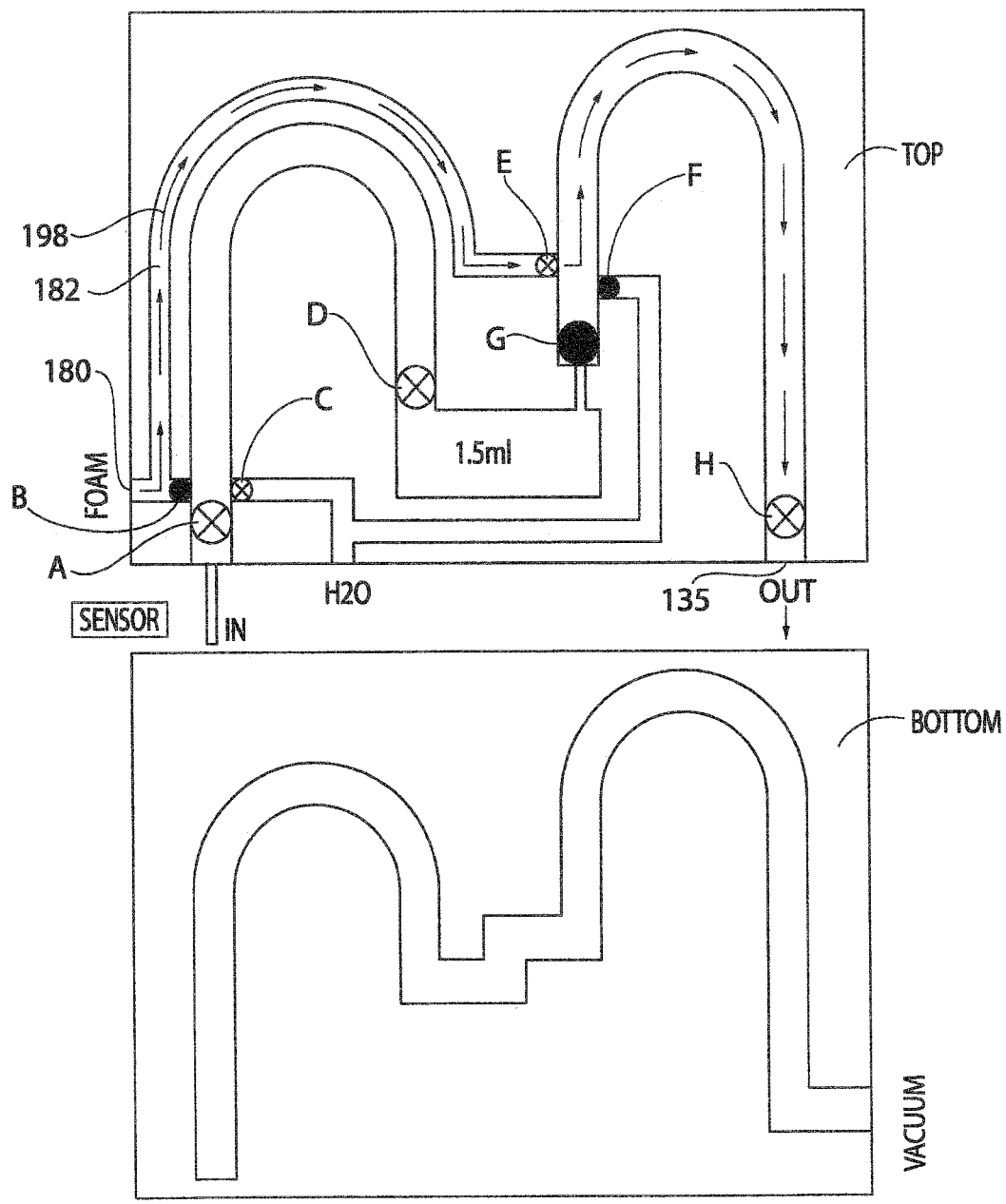
Figure 10B:
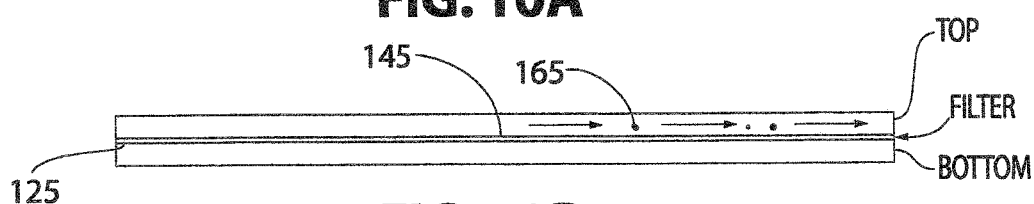

Finally, directing attention to FIGS. 10A and 10B, valves B, G, and F are closed and elution fluid is provided by the foam inlet 180 along the foam channel 182, as indicated by arrows 198. Just as before, the elution fluid moves transversely across the upper surface 145 of the filter element 125 and scrapes the particles 165 from the upper surface 145 of the filter element 125, where they are then transported through the outlet 135 into a secondary collector to provide a fluid/particle mixture, wherein the fluid has an exceptionally low fluid volume relative to the particle concentration, thereby allowing analysis of the particles to proceed with greater ease.

Overall, FIGS. 5-10 illustrate the filter arrangement 110 for isolating particles 165 from a fluid/particle mixture. The filter arrangement is made of a top element 115 having at least one open 60 channel extending thereacross connecting a top element inlet 130 to a first collector 185, wherein the channel 160 is open on the underside 147 of the top element 115. A bottom element 120 having at least one open channel 150 extending thereacross connected to a bottom element outlet, or suction outlet 140. The channel 150 is open on the upper side 152 of the bottom element 120. The top element 115 is secured to the bottom element 120 such that the underside 147 of the top element 115 is secured against the upper side 152 of the bottom element 120 and wherein the channels 160, 150 align with one another. The filter element 125 is generally flat and is positioned between the top element 115 and the bottom element 120 and overlaps with the channels 160, 150.

The top element inlet 130 of the filter arrangement 110 is connected to a fluid/particle supply and also top element inlet 180 which is connected to an elution fluid supply, wherein the bottom element outlet 140 is connected to a suction supply. As discussed, the filter arrangement provides a valve arrangement with at least two flow configurations.

With suction applied to the bottom element outlet 140, the fluid/particle mixture is introduced into the top channel 160 and over the filter element 125 thereby depositing retentate particles 165 upon the filter element 125 and passing permeate particles through the filter element 125. Thereafter, with suction discontinued to the bottom element outlet 140, the elution fluid is introduced into the top channel 160 and over the filter element 125 such that the retentate particles deposited upon the filter element 125 are tangentially rinsed and collected through the top element outlet 135 into a first collector 185.

A second collector may be positioned within the path of the open channel 160 of the top element 115 to define a first stage channel 160 on one side of the first collector 185 and a second stage channel on the other side of the first collector 185. The valve arrangement described with respect to the first collector 185 for the first stage channel is repeated for the second stage channel thereby providing a two-stage filter arrangement with retentate initially deposited within the first collector and thereafter finally being deposited within the second collector.

Prior to introducing the elution fluid and after introducing the fluid/particle mixture, with suction applied to the bottom element outlet 140, the rinsing solution is introduced into the top channel 160 and through the filter element 125.

What has so far been described is a filter arrangement utilizing on/off valves A-H to provide different configurations of the subject filter arrangement. In an alternate embodiment, certain of the valves A-H illustrated in FIGS. 5A-10A may be replaced with check valves since there is flow in only a single direction through certain valves. By substituting check valves for these on/off valves where possible, the number of controlled elements may be reduced, thereby not only making control of the filter arrangement easier, but such check valves are less expensive than the on/off valves and, as a result, it is possible to fabricate a disposable filter arrangement that will cost less.

The reference characters associated with the elements in FIG. 11A and FIG. 11B are similar to those reference characters found in FIGS. 5A and 5B, for example, with the exception, however, that each of the valve identifiers, while utilizing the same capital letter, introduces the suffix "1" while the other elements utilize a suffix "A" or, in the event the previous element has now been made into two parts, the suffix "B" will also be used.

FIGS. 11A and 11B include a first bottom channel 150A and a second bottom channel 150B as opposed to a single bottom channel 150 illustrated in FIG. 5A. Additionally, each bottom channel 150A, 150B includes a suction outlet 140A, 140B to direct fluid in the direction indicated by arrows 167A, 167B, respectively. Additionally, FIG. 11A includes a first foam inlet 180A and a second foam inlet 180B as opposed to a single foam inlet 180. FIG. 11A includes two separate water inlets 170A, 170B. By enabling different elution/rinsing fluids within each of the two water inlets 170A, 170B and foam inlets 180A, 180B, it is possible to enable different elution and rinsing fluids in a first cycle and in a separate second cycle. This will allow buffer exchange between the first cycle and the second cycle. Additionally, through the use of separate suction outlets 140A, 140B, it is possible for the second suction outlet 140B to be used to draw the elution fluid into the second chamber.

Directing attention to FIG. 11A, while valves A1-H1 are illustrated in the top element 115A, it should be appreciated that valves A1-C1 and E1-G1 are check valves, while valves D1 and H1 are on/off valves. For those lines in which flow occurs only in a single direction, the inventor has realized that a single check valve may be substituted for an on/off valve, thereby relieving the operator of the duty of adjusting a valve for operation.

As previously discussed with respect to FIGS. 5A-9A, the filter arrangement 110 may be configured for six separate stages. These stages will hereinafter be referred to as: 1) aspirate sample; 2) first rinse; 3) first extraction; 4) second aspiration; 5) second rinse; and 6) final extraction.

For the initial configuration to aspirate the sample, the fluid/particle mixture is introduced through the inlet 130A and travels through the first stage channel 160A. Valve D1 is closed and the vacuum is activated such that the suction outlet 140A draws a vacuum through the bottom channel 150A, thereby depositing particles 165. With particles 165A deposited upon the upper surface 145A of the filter 125A, the first rinse stage begins. Water is introduced at water inlet 170A through check valve C1 and into the first stage channel 160A while the suction provided by the suction outlet 140A pulls the water/particle mixture through the filter 125A filtering additional particles that may not have been filtered during the initial step. The vacuum from the suction outlet 140A is discontinued and the on/off valve D1 is opened. At this point, elution is introduced under pressure at the foam inlet 180A where the liquid proceeds past the check valve B1 into the first stage channel 160A where it wipes the particles 165 from the top upper surface 145A of the filter element 125A into the collector 185A.

Any positive pressure that may be caused by the elution foam breaking down into a liquid may be vented through check valve G1.

At this point, the second aspiration stage begins with vacuum provided at the suction outlet 140B and valve H1 in the closed position. The particle/liquid solution is drawn from the collector 185A and past valve G1 into the second stage channel 190A where it then passes through the filter element 125A into the bottom channel 150B where the elution fluid and undersized particles are removed while the oversized particles 165A remain on the upper surface 145A of the filter element 125A.

In the second rinse stage, the suction outlet 140B is still energized but water is now introduced into the second stage channel 190A through the water inlet 170B. The water is pulled through the filter 125A and washes additional particles from the upper surface 145A of the filter element 125A through the suction outlet 140B where it is disposed.

The last stage is the final extraction, whereby there is no suction provided through the bottom channel 150B but elution fluid is introduced through foam inlet 180B where it travels into the second stage channel 190A. Valve H1 is open such that the elution fluid displaces the particles 165A from the upper surface 145A of the filter element 125A and moves them past the open valve Ell into a final receptacle (not shown). By doing this, particles are provided in a relatively low volume elution fluid which thereafter may be further analyzed with greater ease.

The embodiment just discussed in general replaced a number of on/off valves with check valves to make control of the multiple stages of the filter arrangement easier and to reduce costs.

FIGS. 12A-17A and 12B-17B illustrate yet another embodiment, whereby a series of three-way stopcock valves M, N, O, P are utilized to configure the filter arrangement for different stages. Once again, the discussion will be directed to the six stages previously discussed including: 1) aspirate sample; 2) first rinse; 3) first extraction; 4) second aspiration; 5) second rinse; and 6) final extraction.

Figures 12A, 12B:
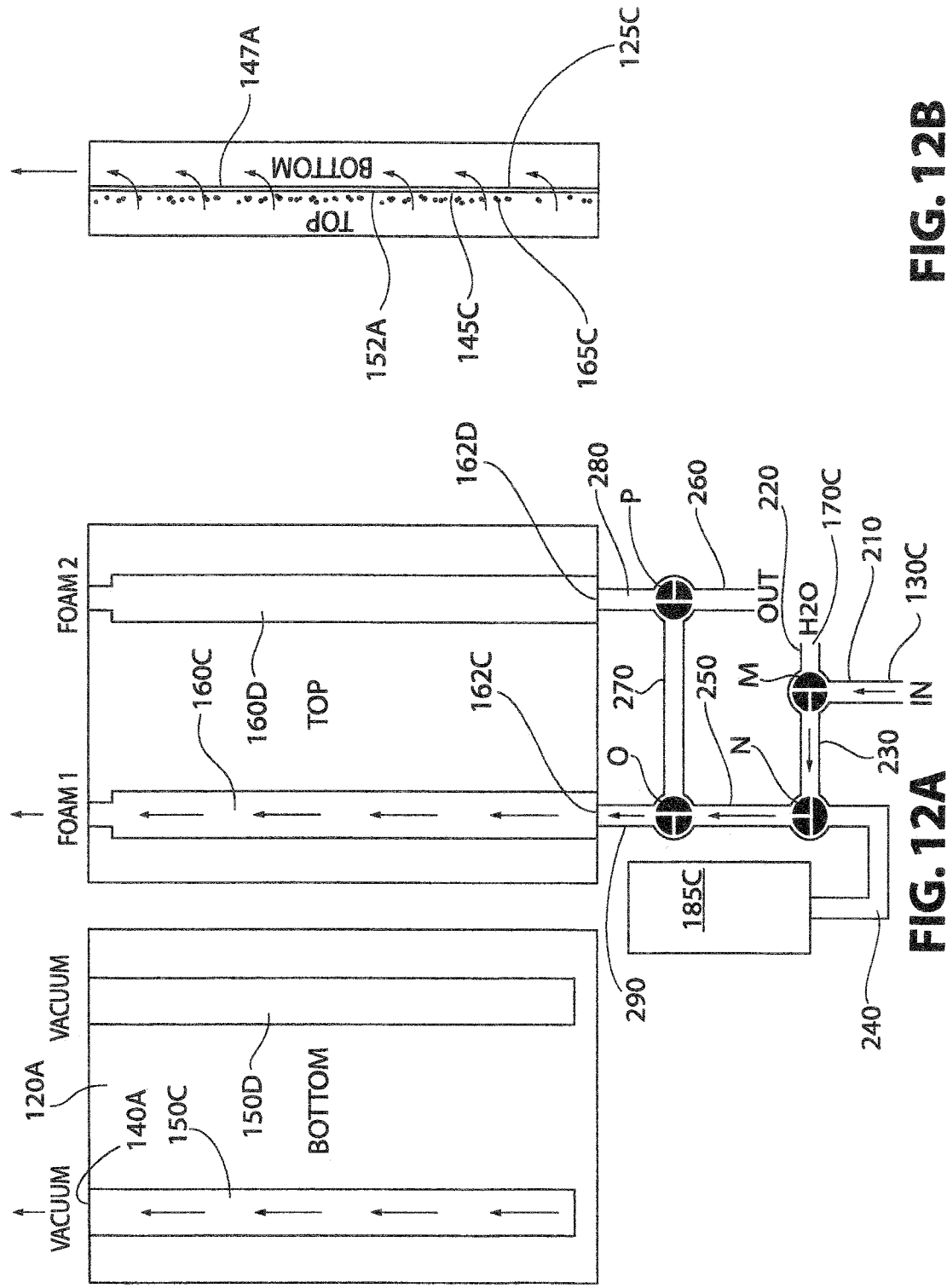

FIGS. 12A and 12B are directed to the stage of aspirating the sample, wherein the bacteria sample is introduced through inlet 130C and valves M, N, and 0 are oriented such that the flow is directed through passageways 210, 230, 250, and 290 and into the first stage channel 160C. Vacuum is applied to the bottom channel 150C such that particles 165C are retained on the upper surface 145C of the filter element 125C. The liquid and particles that pass through the filter element 125 C are discarded.

Figure 13B:
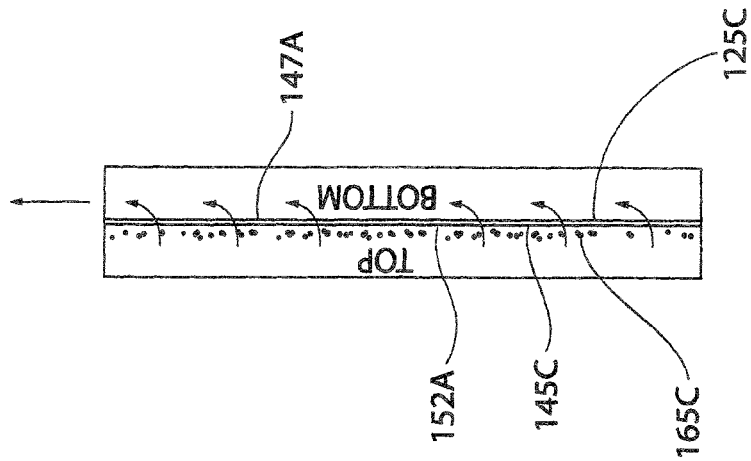
Figure 13A:
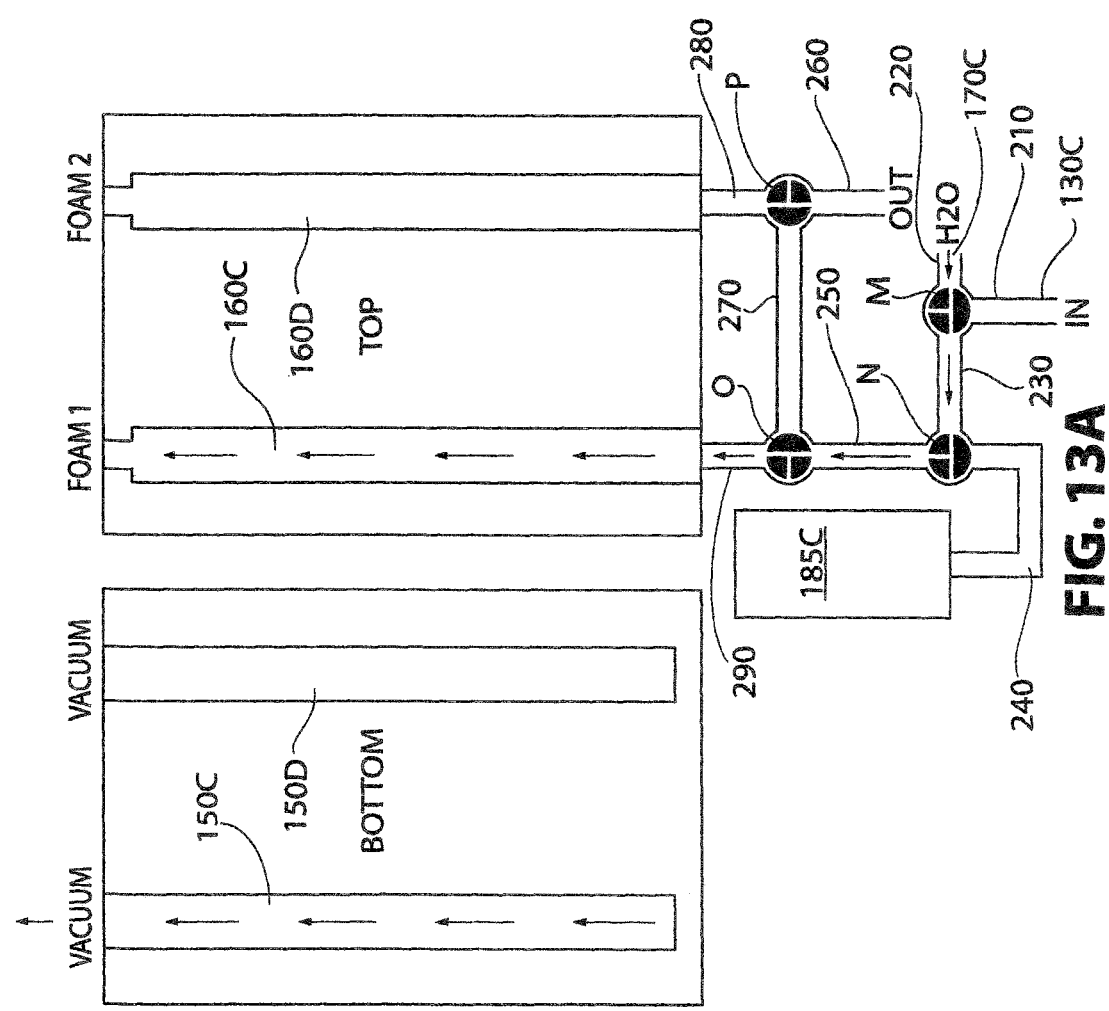
Figures 14A, 14B:
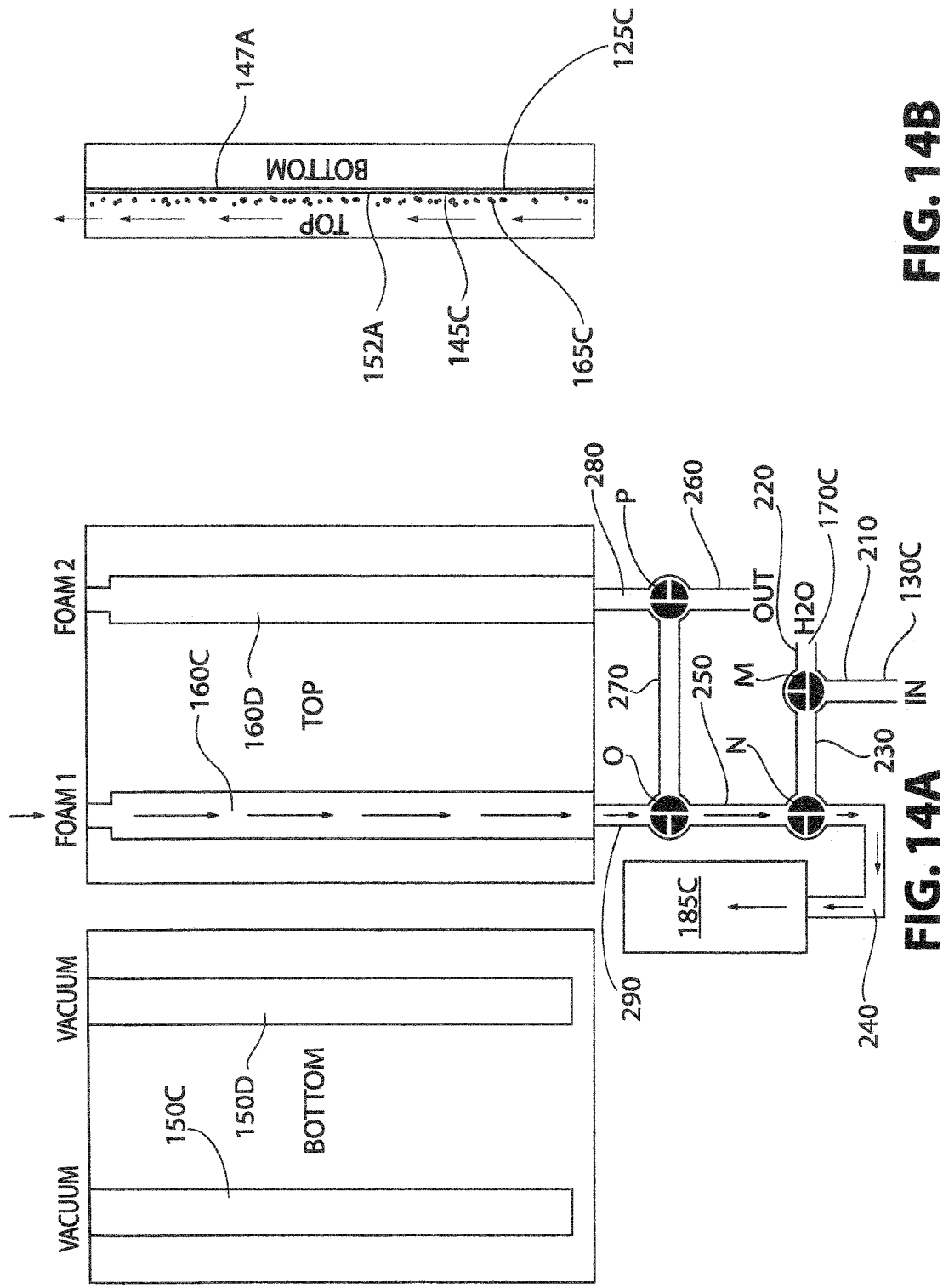
Figures 15A, 15B:
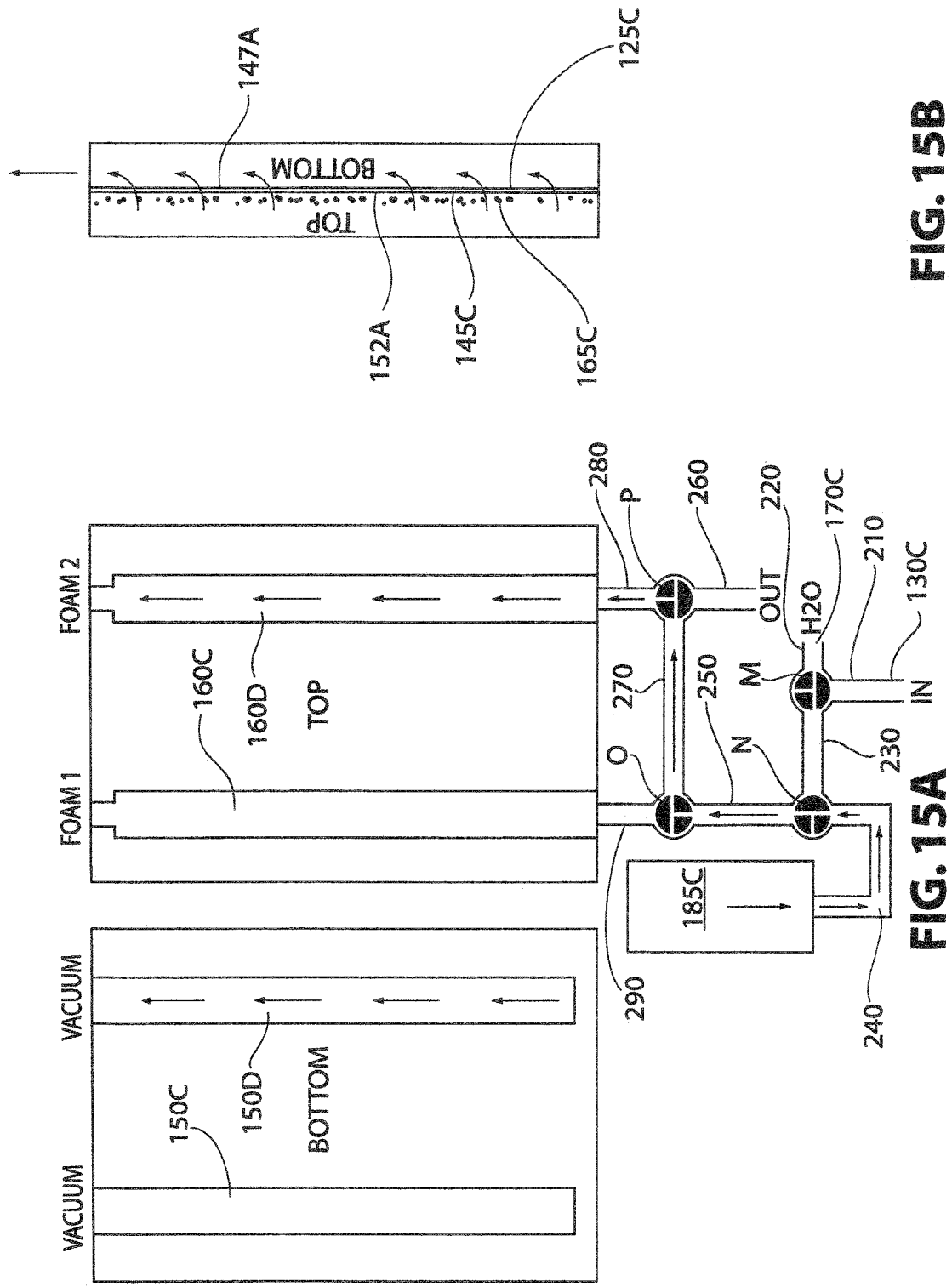

Directing attention to FIGS. 13A and 13B, with the particles 165C retained on the upper surface 145C of the filter element 125C, water is introduced by orienting valves M, N, and 0 such that water enters at the water inlet 170C and travels through passageways 220, 230, 250, and 290 into the first stage channel 160C. With a vacuum applied in bottom channel 150C, the water and undersized particles travel through the filter element 125C and are discarded, thereby providing additional filtering of undersized particles.

With particles 165C deposited upon the upper surface 145C of the filter element 125C, those particles may now be extracted. Directing attention to FIGS. 14A and 14B, elution is introduced through the first stage channel 160C and valves O and N are oriented such that the flow proceeds through passageways 290, 250, and 240 into the collector 185C. The elution moves the particles 165C across the upper surface 145C of the filter element 125C and into the passageway 290. In this manner, a relatively low volume of elution is mixed with the particles 165C and deposited within the collector 185C.

Any positive pressure that may be caused by the elution foam breaking down into a liquid may be vented through the top of the collector, which is open.

The elution/particle mixture now deposited in the collector 185C may be processed through a second filtering procedure which includes a second stage of aspirating. Directing attention to FIGS. 15A and 15B, valves N, 0, and P are oriented such that the elution/particle mixture in the collector 185C through a vacuum applied to the bottom channel 150D, is moved through passageways 240, 250, 270, and 280 into the second stage channel 160D and, once again, particles 165C are deposited on the upper surface 145C of the filter element 125C.

Figure 16B:
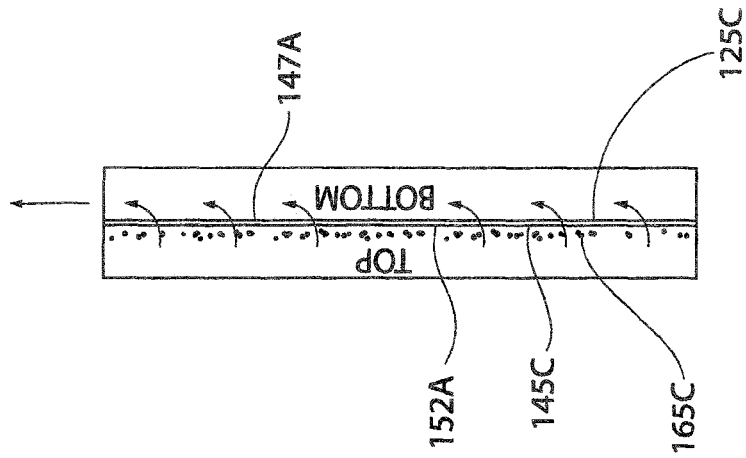
Figure 16A:
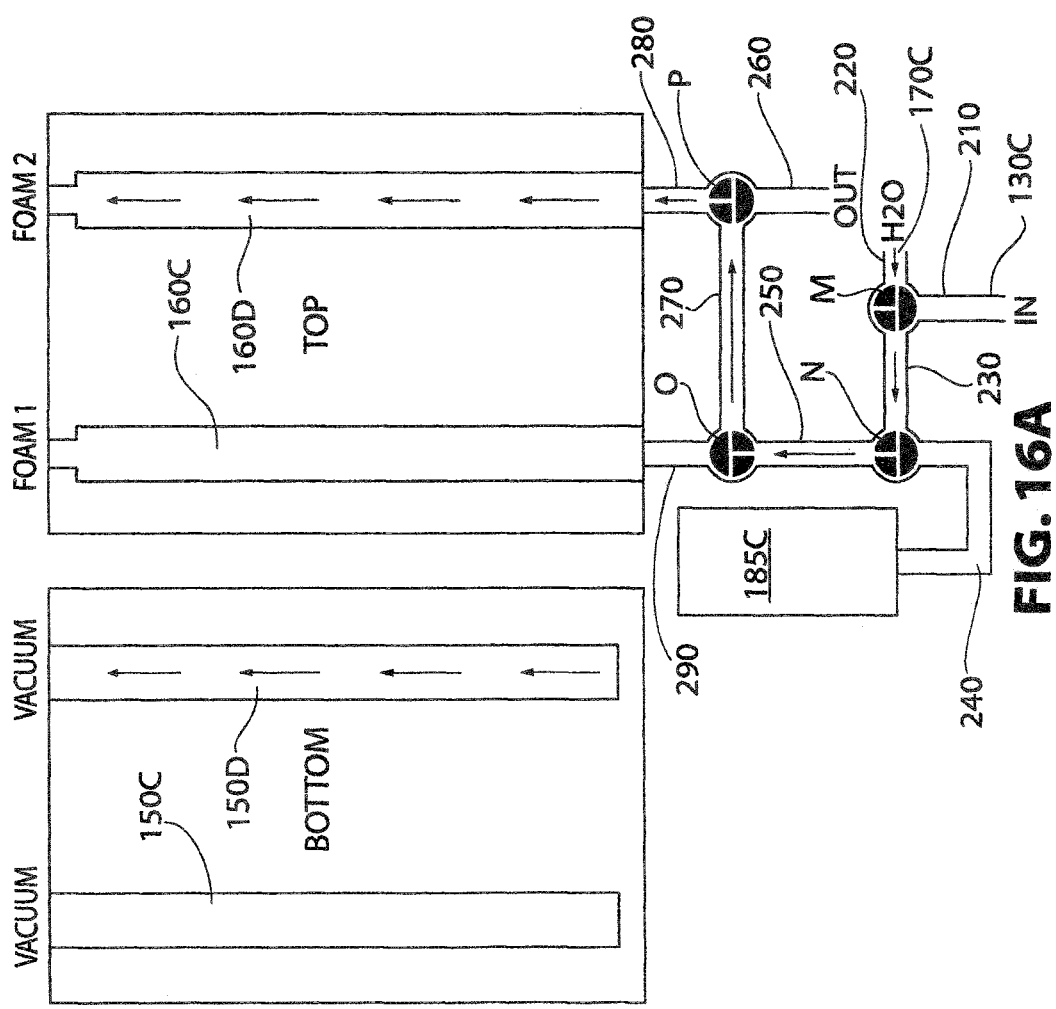

The second rinse stage, illustrated in FIGS. 16A and 16B, may now be initiated. In particular, with valves M, N, O, and P oriented as illustrated, water may be introduced at the water inlet 170C such that it travels through passageways 220, 230, 250, 270, and 280 and into the second stage channel 160D. There the water and smaller particles pass through the filter element 125C and are discarded to provide a better sampling of particles 165C.

Figure 17B:
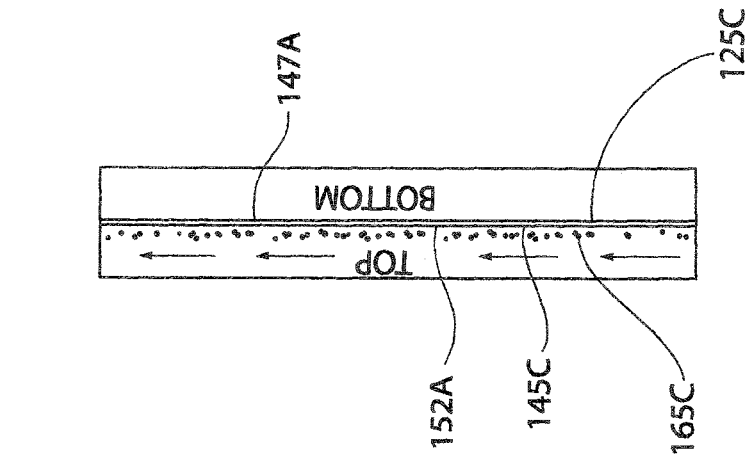
Figure 17A:
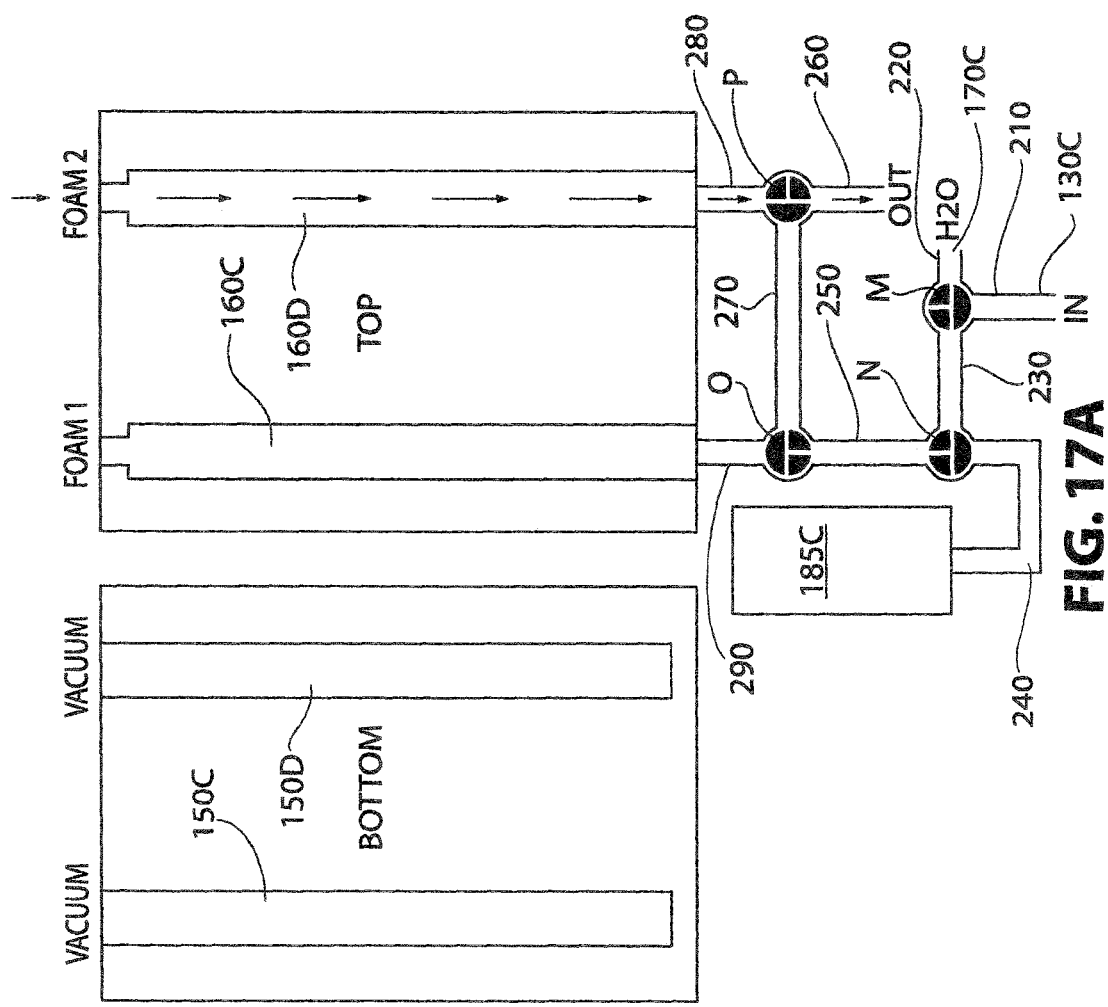

Now the second stage may be completed with a final extract as indicated in FIGS. 17A and 17B. In particular, with the particles 165C deposited upon the upper surface 145C of the filter element 125C, elution under pressure is introduced into the second stage channel 160D, thereby displacing the particles 165C from the upper surface 145C. With valve P oriented as shown, the particles and the elution are washed through the second stage channel 160D into passageway 280 through valve P where they travel through passageway 260 into a final collector (not shown), providing a high quality sample of particles 165C mixed within a relatively low volume of liquid.

FIGS. 12A-17A and 12B-17B illustrate a filter arrangement having two separate channels 160C, 160D each capable of accepting an independent supply of elution and, furthermore, a series of valves M, N, O, and P permit the original particle liquid sample to be directed to either the first stage channel 160C or the second stage channel 160D. Furthermore, this configuration permits water through inlet 170C to be introduced into either the first stage channel 160C or the second stage channel 160D.

Overall, FIGS. 12A-17A and 12B-17B illustrate an alternate filter arrangement for isolating particles 165 from a fluid/particle mixture. The filter arrangement is made of a top element having at least one open 160C channel extending thereacross in fluid communication with a top channel inlet/outlet 162C to a first collector 185C wherein the channel 160C is open on the underside 147A of the top element 115. A bottom element 120A having at least one open channel 150C extending thereacross connected to a bottom element outlet, or suction outlet, 140A. The channel 150C is open on the upper side 152A of the bottom element 120A. The top element 115A is secured to the bottom element 120A such that the underside 147A of the top element 115A is secured against the upper side 152A of the bottom element 120A and wherein the channels 160C, 150C align with one another. The filter element 125A is generally flat and is positioned between the top element 115A and the bottom element 120A and overlaps with the channels 160C, 150C.

The top channel inlet/outlet 162C of channel 160C of the filter arrangement is connected to a fluid/particle supply and an elution fluid supply, wherein the bottom element outlet 140A is connected to a suction supply. As discussed, the filter arrangement provides a valve arrangement with at least two flow configurations.

With suction applied to the bottom element outlet 140A, the fluid/particle mixture is introduced through the top channel inlet/outlet 162C into the top channel 160C and over the filter element 125C thereby depositing retentate particles 65C upon the filter element 125C and passing permeate particles through the filter element 125C. Thereafter, with suction discontinued on the bottom element outlet 140A, the elution fluid is introduced into the top channel 160C and over the filter element 125C such that the retentate particles deposited upon the filter element 125C are tangentially rinsed through the top channel inlet/outlet 162C and collected into collector 85C.

The top element 115C may have a second stage channel 160D extending thereacross in fluid communication with another top channel inlet/outlet 162D to define a first stage channel 160C on one side of the top element 115C and a second stage channel 160D on the other side of the top element 115C such that the valve arrangement described in parts 1) and 2) for the first stage channel 160C is repeated for the second stage channel 160D thereby providing a two-stage filter arrangement with retentate initially deposited within the collector 185C and thereafter being processed again and finally being redeposited within the collector 185 C.

The top element inlet 170C may be connected to a rinsing solution supply. Under these circumstances, the valve arrangement may have an additional configuration.

In particular, prior to introducing the elution fluid and after introducing the fluid/particle mixture, with suction applied to the bottom element outlet 135, the rinsing solution is introduced into the top channel 160D at the top channel inlet/outlet 162D and through the filter element 125C.

Just as before and as described with respect to the first stage channel 160C, the second stage channel 160D may have a similar valve configuration such that the processing of fluid retained in the collector 85C from the first stage channel 160C may be introduced into the second stage channel 160D for further processing and refinement, after which the refined particles are redeposited within the collector 185C.

While predefined steps utilizing this filter arrangement have been described herein, it should be appreciated that depending upon the specific need, there may be a single stage utilized or multiple stages and the individual steps or the sequence of steps may be different.

Figure 18A:
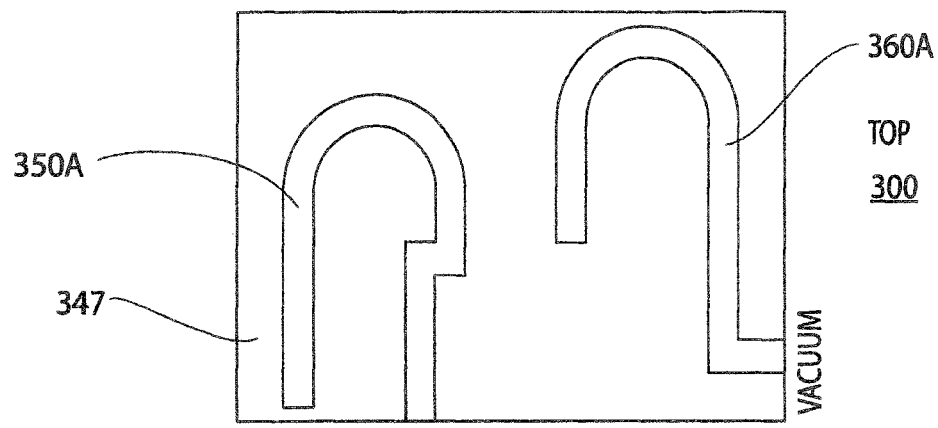
FIG. 18A is a schematic view of a filter arrangement utilizing a sandwiching arrangement, whereby a previously described "top portion" is sandwiched between two "bottom portions" to provide greater filtering capacity.
Figure 18A:
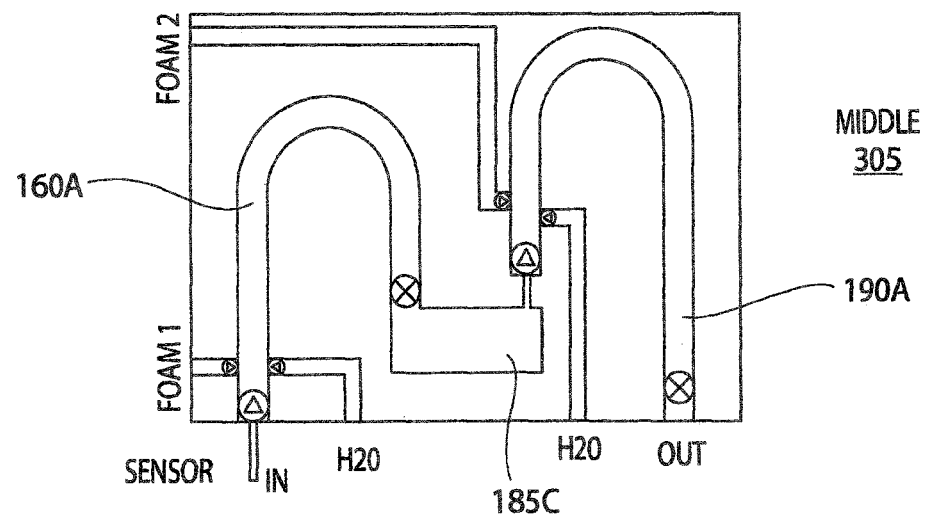
Figure 18A:
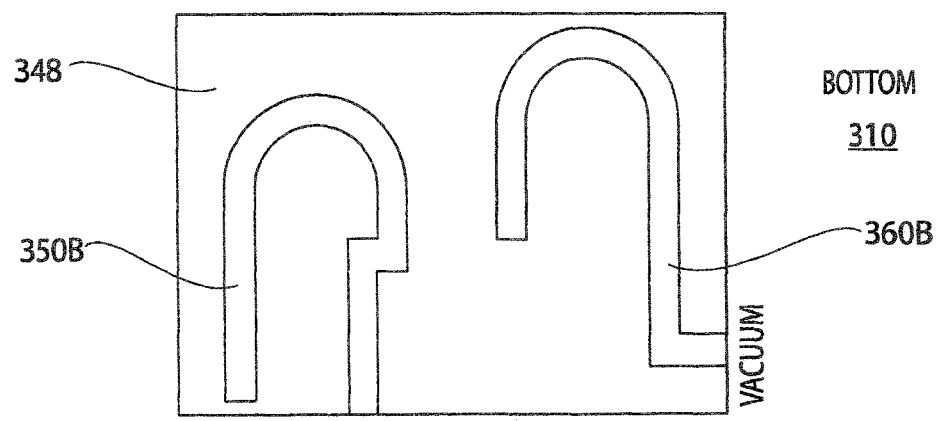
Figure 18B:
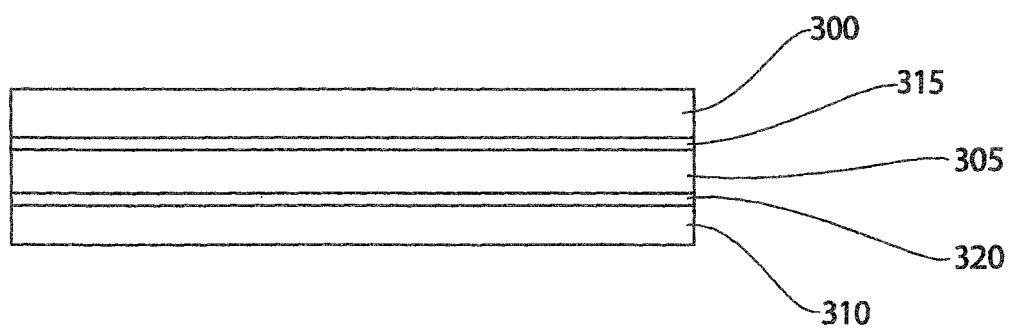
FIG. 18B is a schematic view of the filter arrangement in FIG. 18A in the assembled state.

In a further embodiment, a dual filtering arrangement is possible as illustrated in FIGS. 18A and 18B. In particular, FIG. 18A illustrates a top sandwich element 300 identical to the bottom element 120A illustrated in FIG. 11A and illustrates a middle sandwich element 305 similar to the top element 115A illustrated in 11B. However, the channels 160A, 190A of the middle sandwich element 305 extend completely through the thickness of the middle sandwich element 305. The channels 60A, 190A are in fluid communication with a collector 185C. Furthermore, a bottom sandwich element 310 is identical to the top sandwich element 300. However, the channels 350A, 360A are on the underside 347 of the top sandwich element 300 while the channels 350B, 360B are on the upper side of the bottom sandwich element 310.

Figure 19:
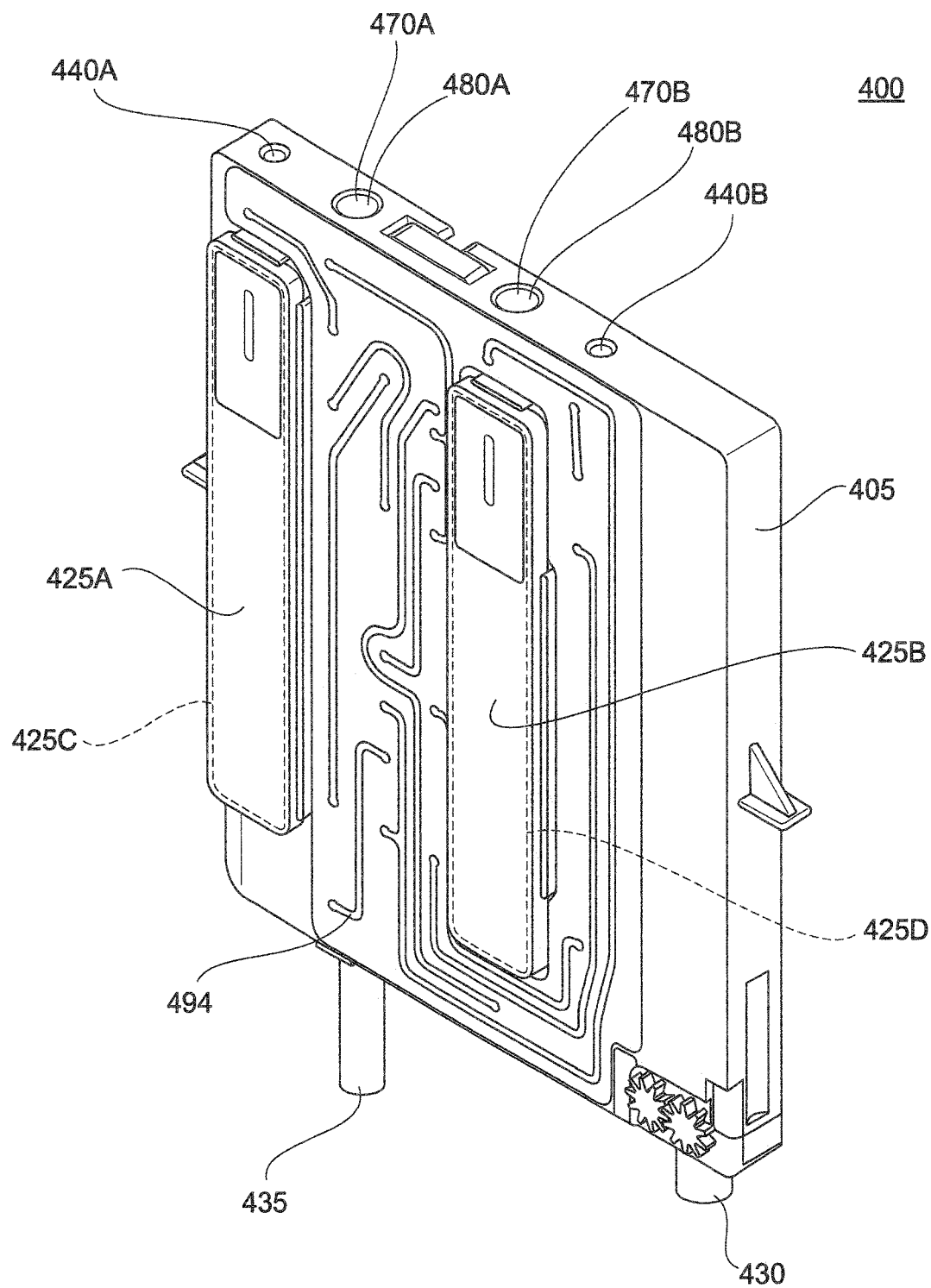
FIG. 19 is a perspective view of yet another embodiment of the filter arrangement utilizing a slider valve to configure different fluid paths.
Figure 20:
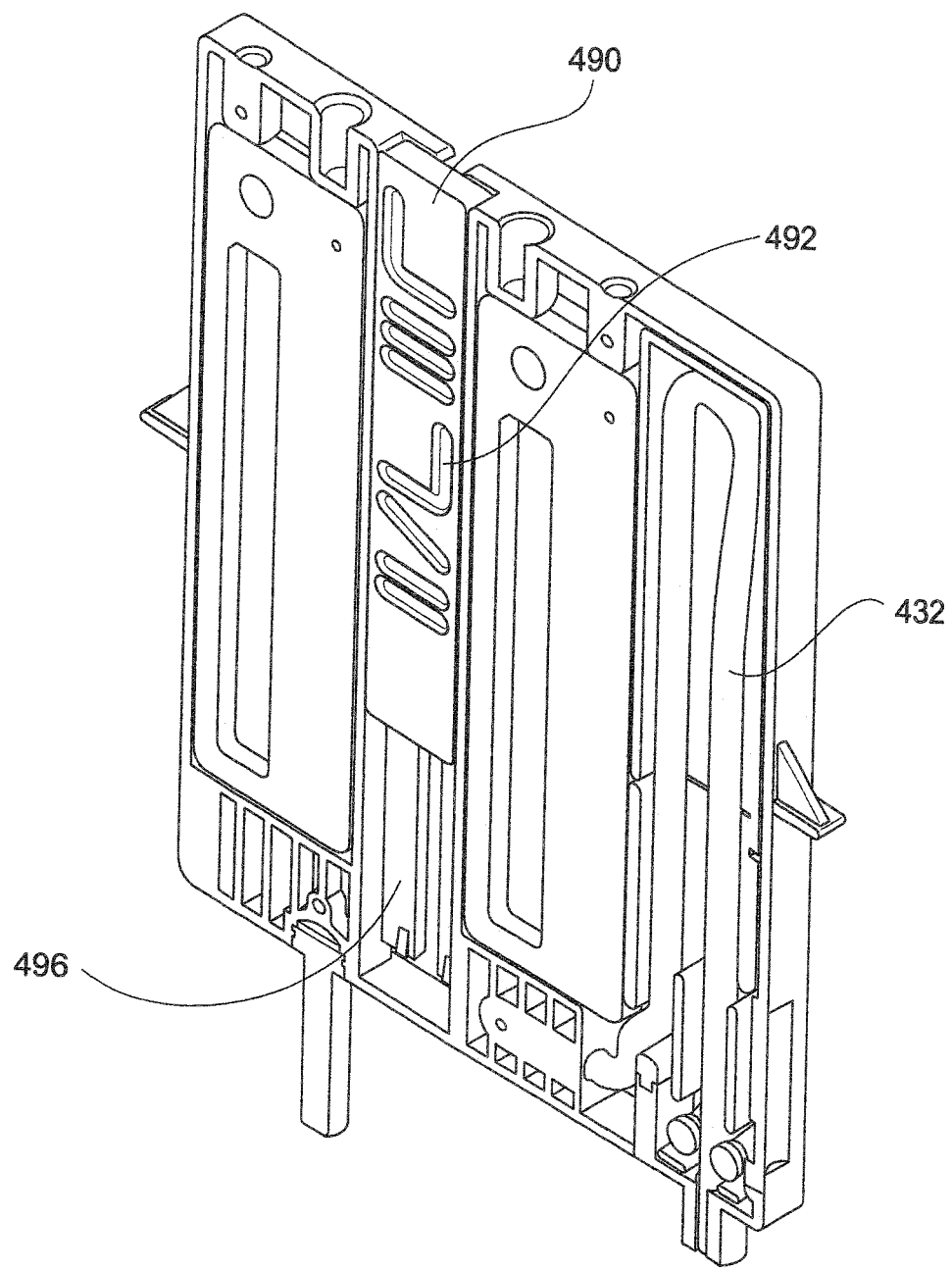
FIG. 20 is a section view of the valve arrangement showing the slider valve.
Figure 21:
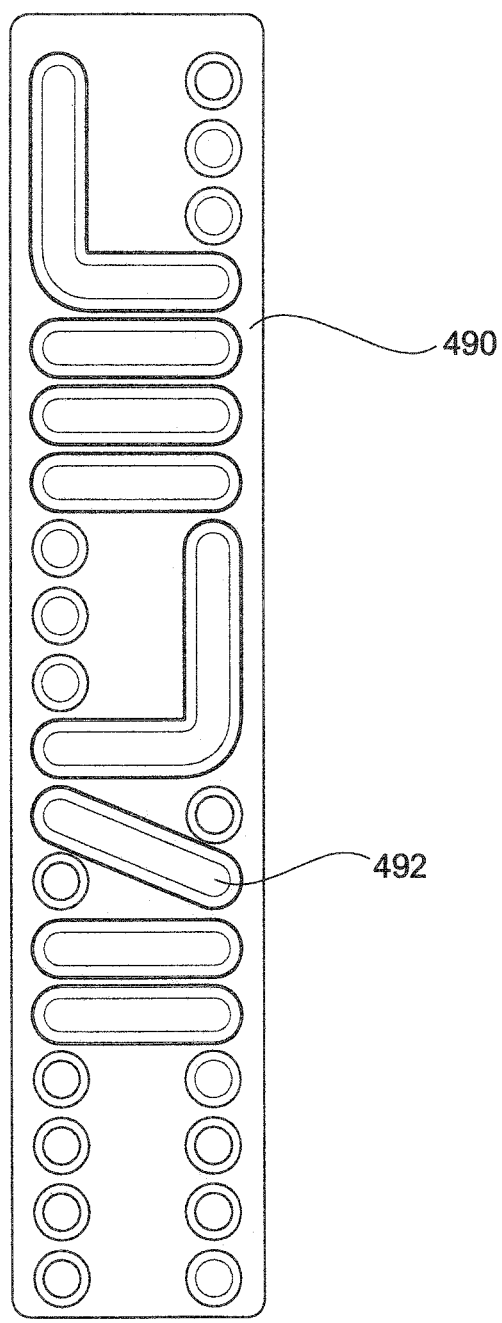
FIG. 21 illustrates details of the slider valve.

As previously discussed, it should be appreciated that the view of the top sandwich element 300 is a transparent view and, in actuality, the channels are on the underside of the top sandwich element 300. Additionally, the channels in the bottom sandwich element 310 are on the upper side of the bottom sandwich element 310 such that, directing attention to FIG. 19, when the top sandwich element 300, the middle sandwich element 305, and the bottom sandwich element 310 are placed together, the channels are aligned with one another. Placed between the top sandwich element 300 and the middle sandwich element 305 is a top filter element 315 and placed between the middle sandwich element 305 and the bottom sandwich element 310 is a bottom filter element 320. By utilizing this configuration, the top filter element 315 and the bottom filter element 320 provide twice the membrane surface with the same channel volume.

Any positive pressure that may be caused by the elution foam breaking down into liquid may be vented through the check valve immediately downstream of the collector 185C.

Additionally, the filter elements discussed herein may be made up of a hydrophobic membrane to allow the passage of trapped air to the vacuum side.

Finally, a flow sensor may be added to the vacuum side to sense when all of the sample has been aspirated, thereby alleviating the need to have a sensor on the "clean side" of the disposable filter.

Figure 22:
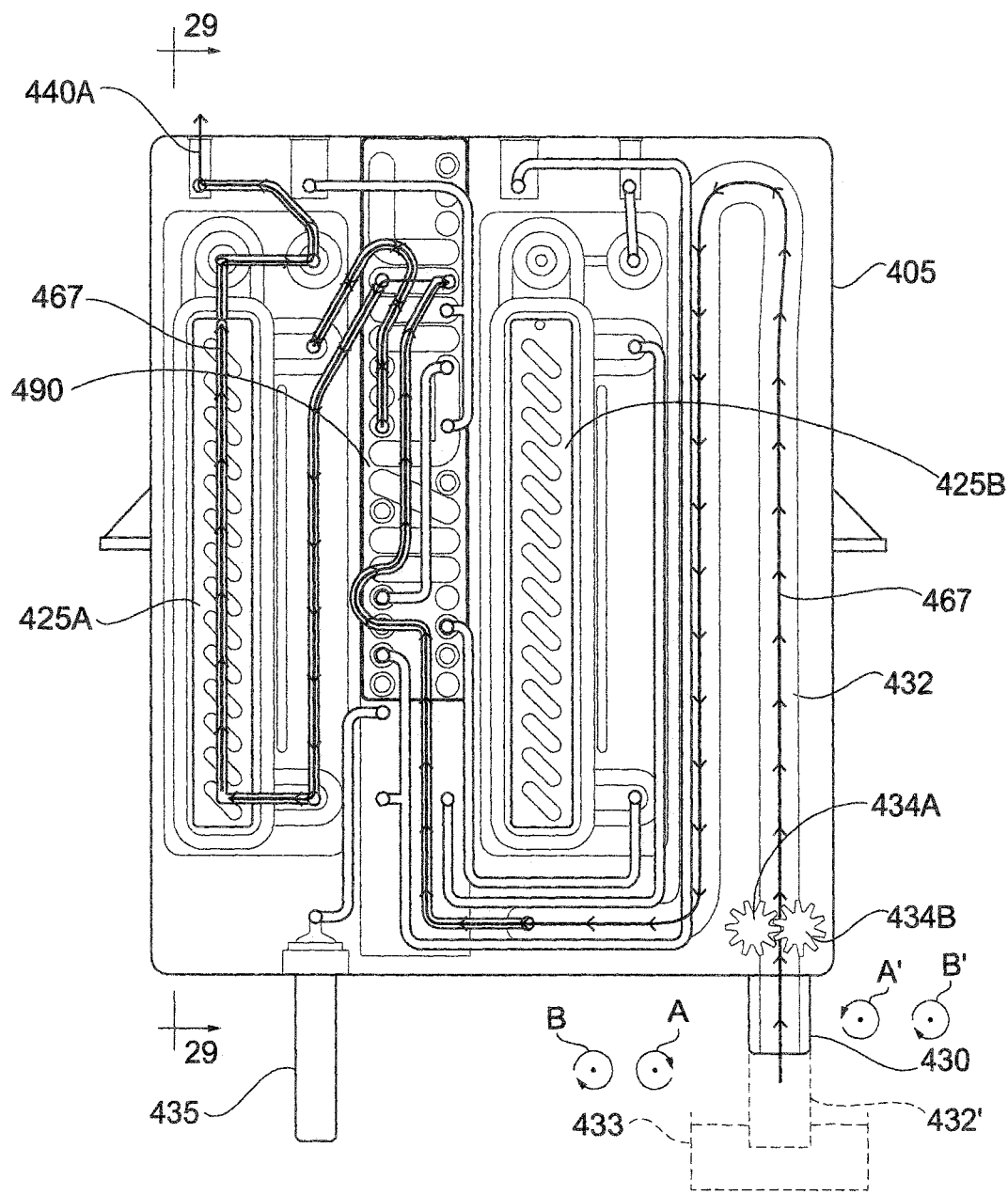
FIGS. 22-28 are schematic views of yet another embodiment of the filter arrangement illustrating different configurations for the filtering process and, furthermore, utilizing a slider valve configure different fluid paths.

The method disclosed herein provides for the use of wet foam to remove microorganisms from a membrane surface and resuspend them in a fluid of choice. It is also possible to provide high recovery for low concentration specimens while maintaining consistency regardless of the specimen source.

The filter element provides 0.4 micron filtration of permeate and removes proteins, soluble materials and cell fractions. Additionally, by rinsing the filter element with rinsing solution, it is possible to remove small surface hanging particles and droplets from the original matrix while the use of wet foam allows extraction of the microorganisms from the surface of the filter.

Through the use of foam, which may be 80-90% gas, during the foam extraction the empty space is filled without contributing to the final sample volume. Additionally, the foam has a higher viscosity which prevents channeling and creates a more uniform flow across the filter surface. The foam produces micro bubbles which behave as deformable solids, effectively squeegeeing the particles off of the surface of the filter element. Overall, the filter based separation of particles in combination with the wet foam extraction into a matrix provides a superior filtering system.

FIGS. 19-28 illustrate yet another embodiment similar to that embodiment described with respect to FIGS. 12-17, however the stopcock valves M, N, O, P, which were previously utilized to configure the filter arrangement for different stages, has now been replaced with a linear slider valve. Additionally, FIGS. 22A, 23A, 25A, 26A, and 28A are process flow diagrams showing the system in which the cartridges are utilized for the cartridge configurations shown in FIGS. 22-28.

Prior to discussing the individual configurations of a filter arrangement, FIG. 29 will be reviewed, showing a process flow diagram for an entire cluster of filter arrangements. For convenience, different portions of the process flow diagram are labeled with capital letters PA-PH.

Pressurized gas in a pressure vessel PA is introduced to a pressure vessel PB filled with liquid such that the pressurized gas dissolves within the liquid to provide an effervescent liquid. There are two pressurized tanks shown in the process schematic—one with nitrogen and one with carbon dioxide. Nitrogen gas may be preferred because it does not leave any traces within the sample while carbon dioxide may be preferred because it dissolves better in liquid. Nevertheless, the choice of gas selection is up to the user. Pressurized effervescent liquid exits from a pressure vessel PB to be used with filter arrangements. There are valves associated with each of the pressurized gas containers that may be used to relieve pressure in the lines when the system is inactive.

Prior to discussing the filter arrangements, in the lower left of FIG. 29, four rinse/waste bottles PC are illustrated. Each of these bottles is dual purpose in that originally three of the bottles are filled with rinse liquid as temporary supply containers while the fourth bottle is empty as a receiving container. The valve and piping may be arranged such that, for example, rinse liquid transported through the rinse line PD provided by bottle 2 and washed through the filter arrangement is then returned the waste line PE into the empty bottle 1. The valving may now be changed such that rinse liquid may be taken from another bottle, such as bottle 3, and discharged into what was empty bottle 2. In this situation, bottle 1 is re-designated as a receiving container. The clean rinse liquid from bottle 2 has been depleted while the rinse liquid has now filled bottle 1. This toggling arrangement may continue until the clean rinse water from each of the bottles 2, 3, and 4 has been depleted and all but one of the bottles is filled with waste solution. Rinse liquid from the bottles is moved through the rinse line and the waste lines using vacuum generated by the vacuum pump PF. A drain separator PG is used to separate liquid from the vacuum line to the vacuum pump PF.

Each filter arrangement has associated with it vent lines PI to enhance flow over the filters and also to clear the lines from fluid at the end of the process.

While the configuration of valves for the aspiration, rinsing, and extraction step is more complex than in earlier described embodiments, the primary goal of minimizing space with fewer valves is achieved. Additionally, by providing multiple bottles with the intention of utilizing one at a time for water supply and another for waste supply, space for the device may be further reduced.

The filter arrangements illustrated on the top half of the schematic of FIG. 29 utilize the cartridges having disposable dual membrane filters utilizing slider valves to achieve the necessary configurations for filtering.

Attention will now be focused upon a portion of the process diagram focusing upon the configuration of a particular filter cartridge and the process flow associated with that filter cartridge when positioned in different filter configurations.

Just as with previous embodiments, the discussion will be directed to the six stages including 1) first aspiration of sample; 2) first rinse; 3) first extraction; 4) second aspiration of sample; 5) second rinse; and 6) final extraction.

For consistency, reference numbers for similar items will be numbered similarly as in previous embodiments but will be in the 400 series.

FIG. 19 illustrates the filter arrangement 400 having an inlet 430 for the fluid/particle mixture and suction outlets 440A, 440B. Additionally, two rinse liquid inlets 470A, 470B also function as foam inlets 480A, 480B. Outlet 435 is utilized to collect the separated particles. Separate filter elements 425A, 425B, shown in phantom in FIG. 19, are mounted behind covers 425C and 425D and are mounted upon the filter arrangement body 405.

Directing attention to FIGS. 20 and 21, a slider valve 490 is movable within the filter arrangement body 405. Slider valve 490 has configured upon its surface a plurality of different channels 492 which align with a plurality of channels 494 (FIG. 19) within the filter arrangement body 405. Slider valve 490 moves laterally within the slider valve channel 496 (FIG. 20) and may be precisely indexed at different positions to configure the filter arrangement for different stages.

FIG. 22 illustrates the arrangement similar to FIGS. 12A-12B whereby vacuum is applied to the suction outlet 440A and the fluid/particle mixture is drawn in through the inlet 430. Tube 432 associated with the inlet 430 is flexible tubing which is compressed between two rollers (not shown) operated by gears 434A, 434B and are rotatable to extend the inlet 430 away from the body 405 into a container to extract the fluid/particle mixture. Rotation of the gears in a first direction A and A' extends the tube 432 into the downward position as shown in phantom by 432' in FIG. 22 into a container 433, also shown in phantom in FIG. 22, to receive a sample. Rotation of the gears in direction B and B' will retract the flexible tube 432.

In this configuration the fluid/particle mixture is aspirated through the filter element 425A and the residual liquid is removed from the suction outlet 440A such that particles are deposited upon the upper surface for the filter element 425A. The flow path of the fluid is illustrated by arrows 467.

Directing attention to the process flow diagram of FIG. 22A, the inlet 430 of the filter cartridge 400 is submerged within a liquid sample in the container 433. Vacuum pump PF creates a vacuum in line AA which extends into bottle B1 to create a suction therein. The suction extends into waste line BB through the connection with bottle B1. As a result, sample liquid is drawn up through the inlet 430, over the filter element 425A and the waste liquid passes through the filter element 425A and is then discharged through the suction outlet 440A along lines CC into lines BB where the liquid waste is deposited in originally-empty bottle B1 with retentate particles retained within the filter element 425A of the filter cartridge 400.

Figure 23:
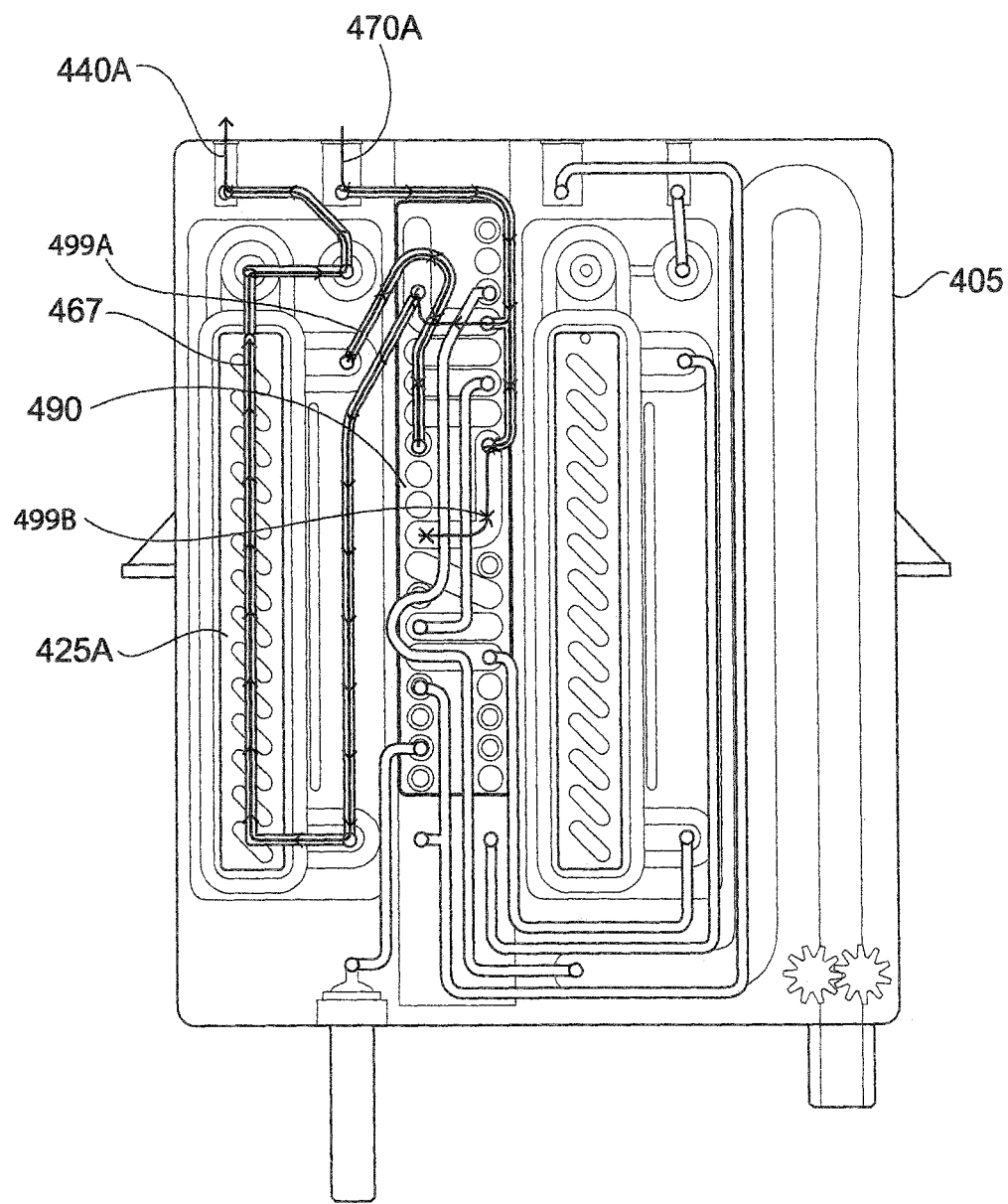

With the particles deposited upon the surface of filter element 425A, slider valve 490 is indexed to a new location as illustrated in FIG. 23 to engage different channels and port in the slider valve 490 and channels 492 in the body 405. Rinsing fluid is now introduced into the rinse inlet 470A and travels along the path illustrated by arrows 467 from inlet 470A through the filter element 425A and exiting through the suction outlet 440A.

Figure 23A:
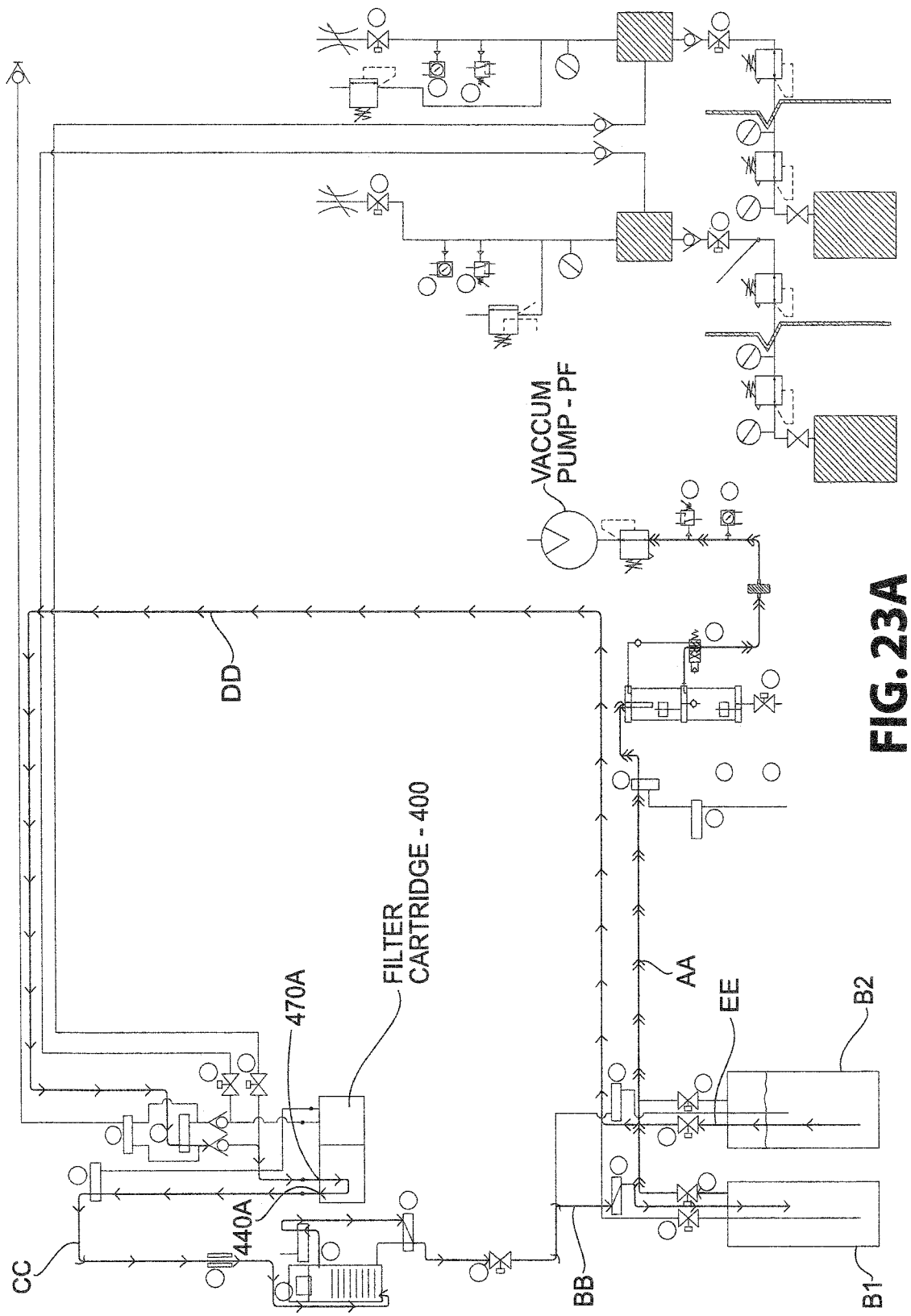

FIG. 23A shows the process flow diagram for the rinse step just described with respect to FIG. 23. In particular, the vacuum pump PF still maintains a suction in line AA which creates a suction in bottle B1 back through line BB to line CC through line DD and into line EE where rinse liquid is extracted from bottle B2 and transported through lines EE and DD to rinse inlet 470A of the filter cartridge 400 where the retained particles are rinsed. The rinse liquid then exits the filter cartridge 400 at the suction of 440A where it proceeds through lines CC and BB and is discharged into bottle B1. Note that in both FIGS. 22A and 23A, rinse liquid is extracted from bottle B2 and discharged into bottle B1.

Utilizing the slider valves in certain indexed positions, the slider valve 490 and the body 405 are aligned such that certain channels that are not utilized in a particular configuration are still connected and thereby receive fluid. As an example, in FIG. 23 channel 499A is exposed to fluid. However, the channel dead-ends and, as a result, fluid accumulates within the channels 499A and 499B. Instead of arrows indicating flow, each of these channels is marked with an "x". To avoid contamination, however, these channels must be cleared and, for that reason, there is a secondary rinse step.

Figure 24:
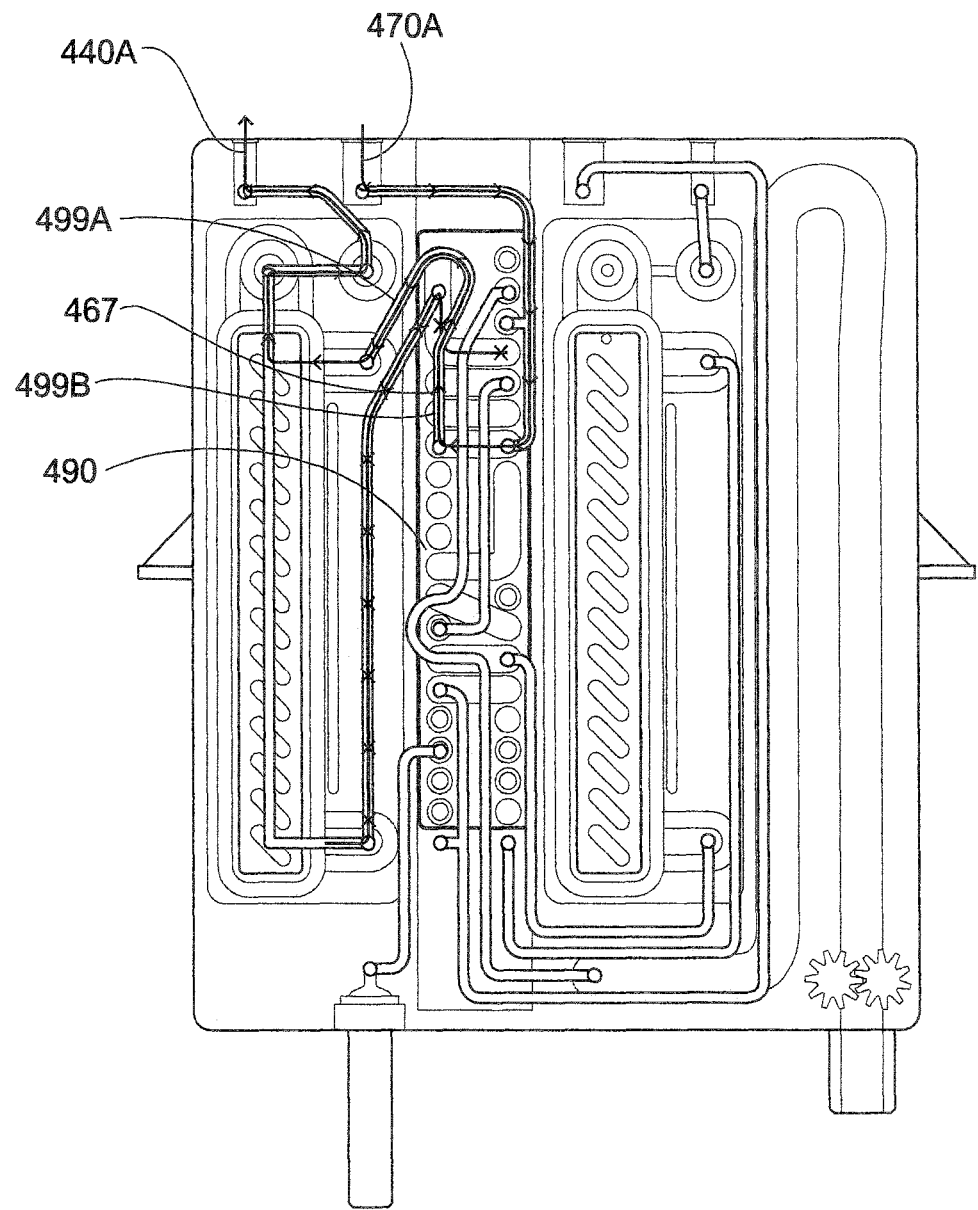

FIG. 24 illustrates this secondary rinse step which exists for the sole purpose of flushing channels 499A, 499B for subsequent processes. In this instance, the slider valve 490 is indexed further down such that inlet 470A conveys fluid and flushes the channels 499A, 499B where the residual fluid is removed through the suction outlet 440A. There is no comparable step described in the previous embodiments.

From an inspection of FIGS. 23 and 24, it should be noted that in each configuration, rinse liquid is provided through inlet 470A and is extracted through the suction outlet 440A. The sole purpose of the arrangement illustrated in FIG. 24 is to purge fluid from the channel dead ends and the external configuration of the filter cartridge 400 is identical. For that reason, the process flow diagram illustrated in FIG. 23A, discussed with respect to FIG. 23, applies equally to the filter configuration found in FIG. 24 and a separate process flow diagram is not included herewith.

Figure 25:
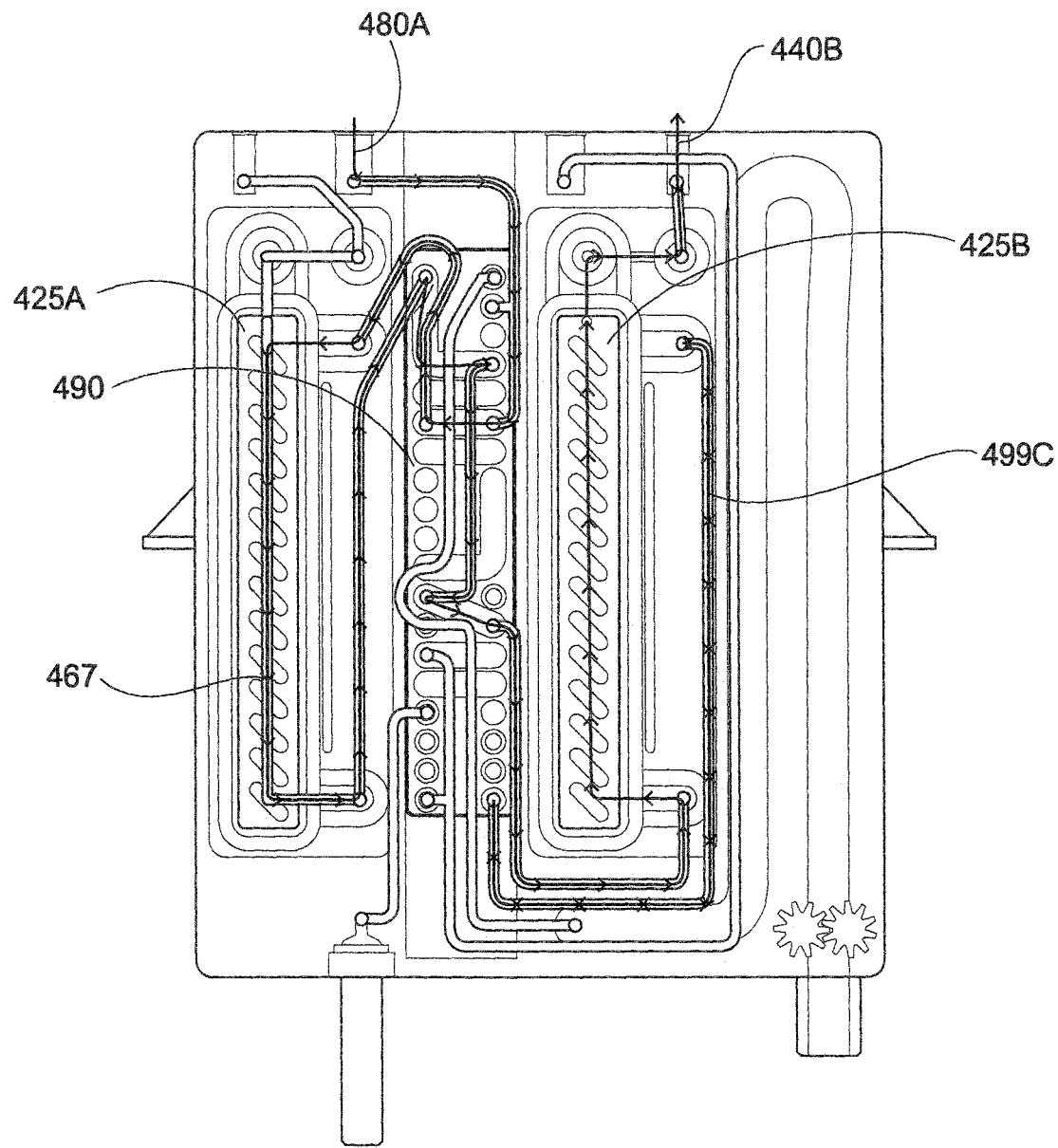

With the channels clear and the particles deposited upon the filter element 425A, as illustrated in FIG. 25, the slider valve 490 is once again indexed to engage a series of different ports and channels such that foam is now introduced into the foam inlet 480A and follows the path indicated by arrows 467 and over the top of the filter element 425A; and particles are removed from the top of the filter element 425A and deposited upon the top of the filter element 425B with the residual foam exiting at the suction outlet 440B. This arrangement is similar to that shown in FIGS. 14A-14B of the previous embodiment but, furthermore, encompasses the configuration illustrated in FIGS. 15A-15B whereby particles aspirated from the top surface of the filter 425A are removed therefrom and deposited upon the top surface of filter element 425B. The foam passes through the filter element 425B where it breaks down into a liquid and is discharged through suction outlet 440B. Unlike the previous embodiment, there is no intermediate reservoir in this configuration. It should be noted in this configuration that the rinse inlet 470A and the foam inlet 480A are the same. Briefly directing attention to FIG. 22, enlargement "A" shows details of this inlet. Note that feature C highlights that the profile of the inlet port is conical. The conical port gives a good seal without the use of elastomers. This conical seal is based upon the same principal as Luer ports seen in syringes.

Figure 25A:
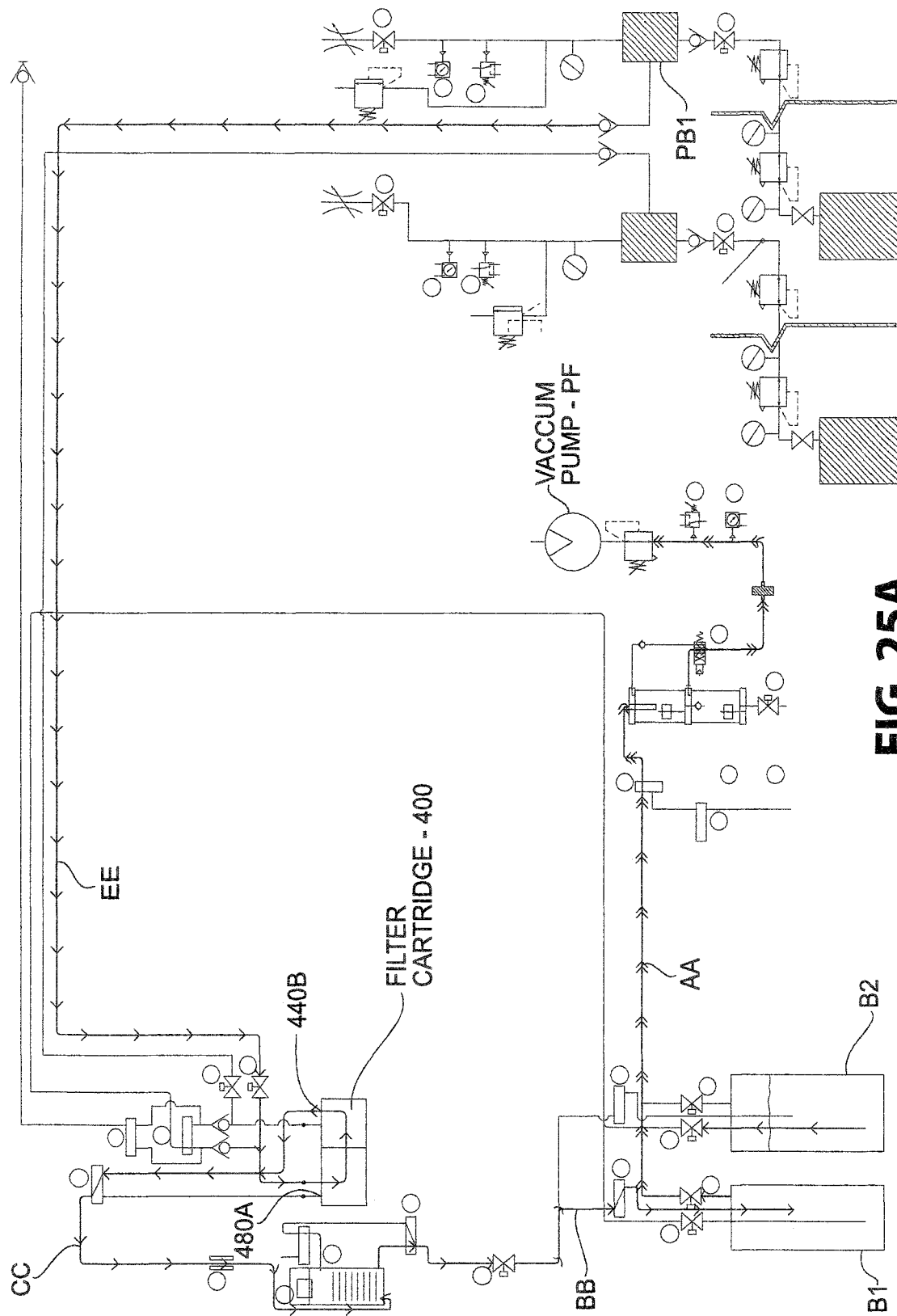

FIG. 25A illustrates the process flow diagram associated with the configuration just described with respect to FIG. 25. In particular, foam is provided from the pressure vessel PB1 through lines EE where it is introduced at the foam inlet 480A over the face of the filter element. Displaced particles from the filter element are then deposited upon the face of the filter element at which time the foam is reduced to a liquid to which exits at the vacuum outlet 440B and travels through lines CC and BB to be deposited in bottle B1. While the pressure of the foam may be sufficient to move the liquid from suction outlet 440B into bottle B1 without the vacuum suction, to make the process more efficient, the vacuum pump maintains suction through line AA into bottle B1 to enhance the flow of the liquid into bottle B1.

Figure 26:
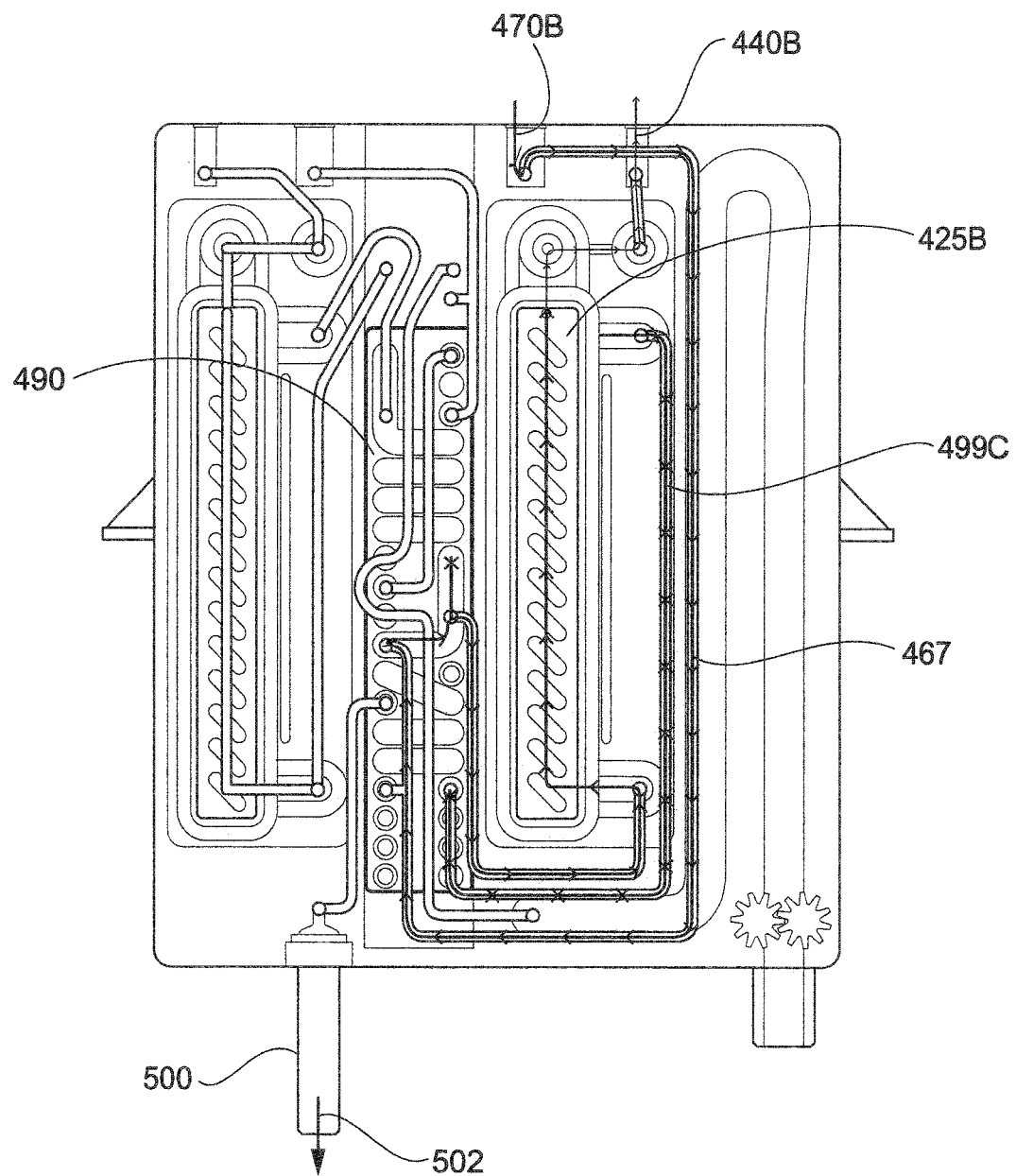

Thereafter, as illustrated in FIG. 26, rinse fluid is introduced at inlet 470B and follows the path indicated by arrows 467 and to rinse the top surface of the filter element 425B wherein the residual fluid is removed at the suction outlet 440B. This arrangement is equivalent to the arrangement illustrated in FIGS. 16A-16B.

Figure 26A:
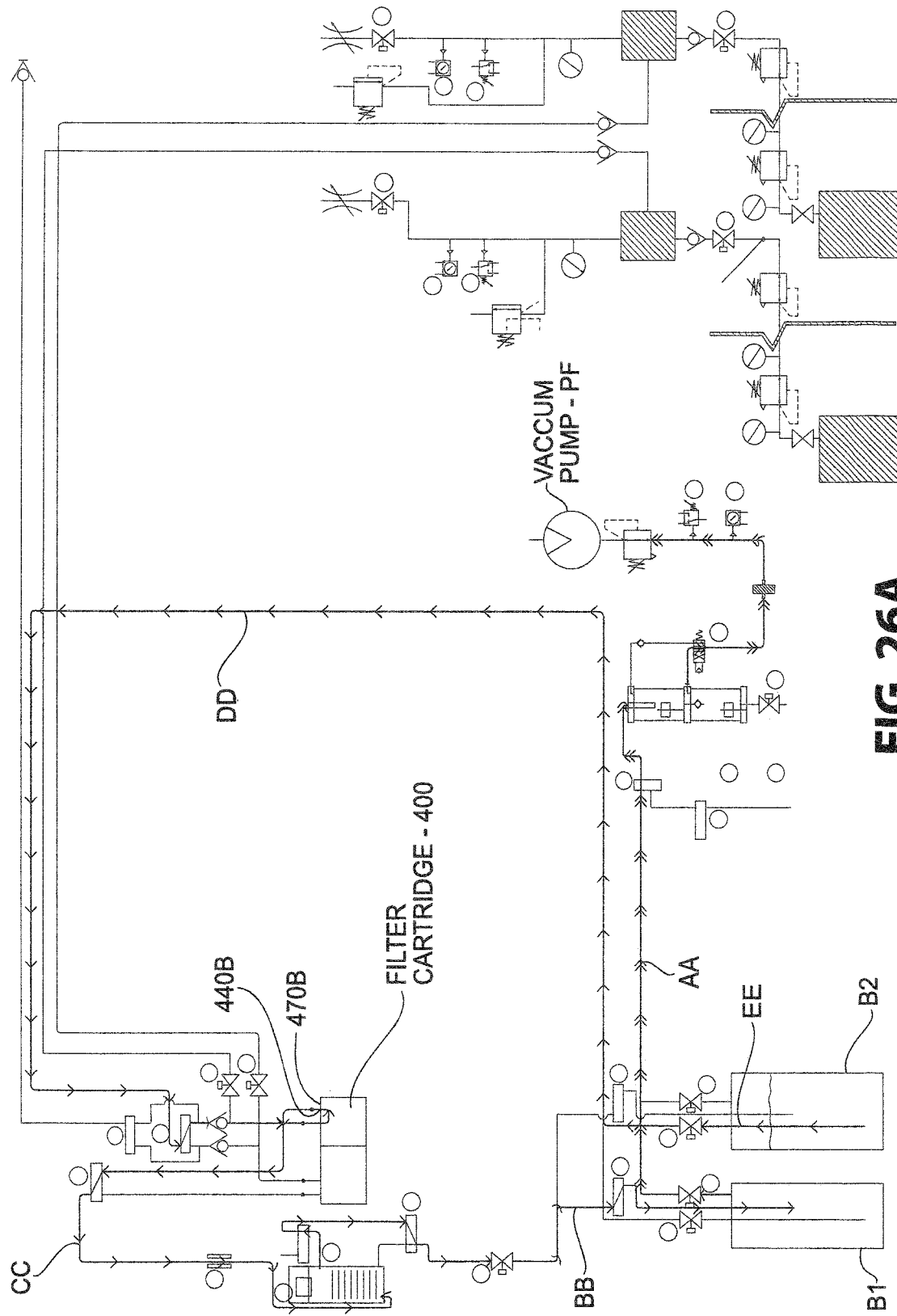

FIG. 26A shows the process flow for the rinse step just described with respect to FIG. 26. In particular, the vacuum pump PF still maintains a suction in line AA which creates a suction in bottle B1 back through line BB to line CC through line DD and into line EE, where rinse liquid is extracted from bottle B2 and transported through lines EE and DD to liquid inlet 470B of the filter cartridge 400, where the retained particles are rinsed and the rinse liquid exits the filter cartridge 400 at the suction of 440B, where it proceeds through lines CC and BB and is discharged into bottle B1. Note again that in both FIGS. 22A and 23A, rinse liquid is extracted from bottle B2 and discharged into bottle B1.

Briefly returning to FIG. 26, note channel 499C does not have continuous flow and the fluid therein becomes stagnant. This channel is marked by "x" and a second rinse step is now required to purge this fluid.

Figure 27:
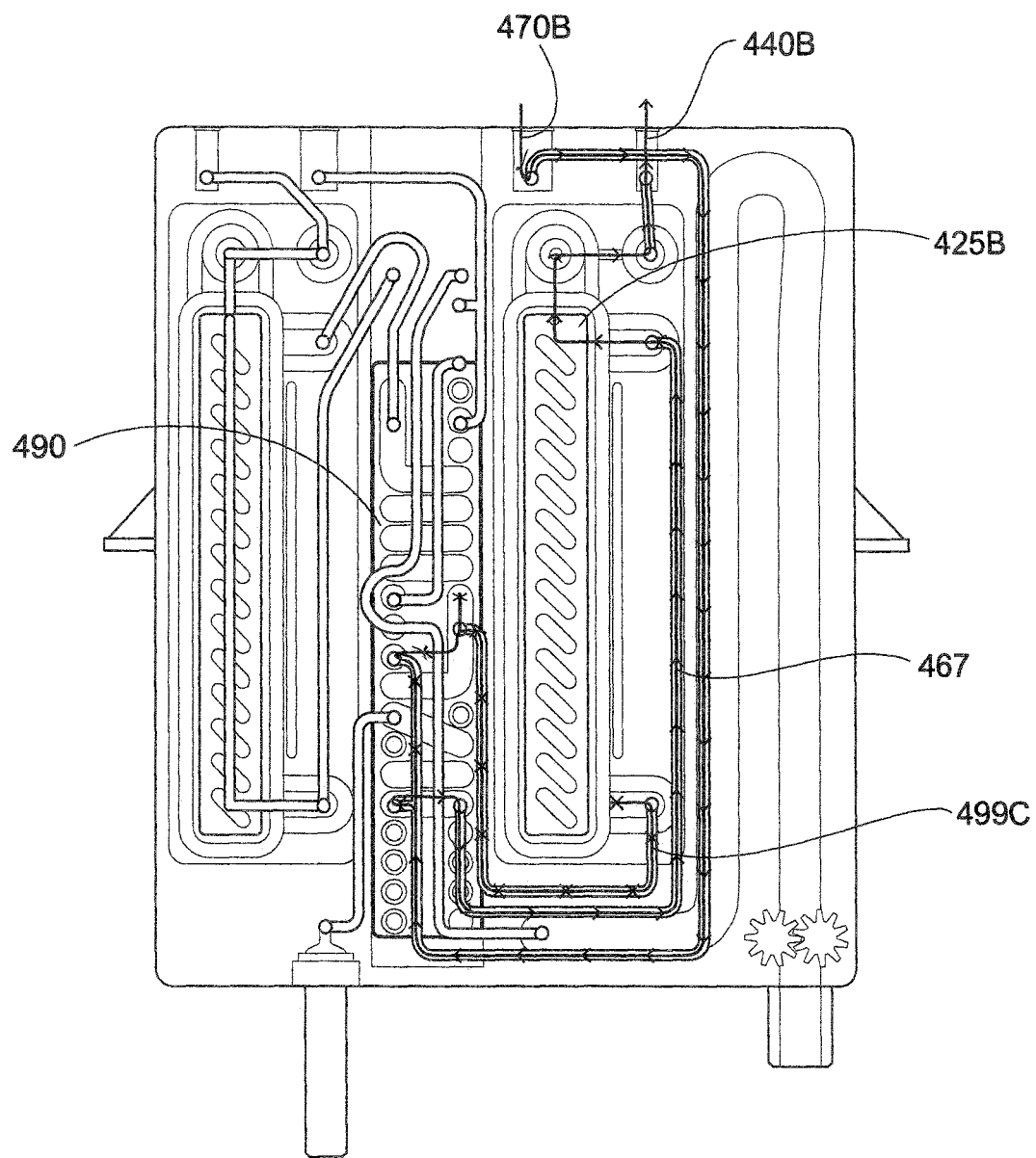

FIG. 27 is a secondary rinse step not found in the previous embodiments whereby the slider valve is further indexed such that now water is still introduced at inlet 470B. Slider valve 490 is indexed such that channel 499C is flushed with rinsing fluid which travels in the direction of arrow 467 and exits at the vacuum outlet 440B.

From an inspection of FIGS. 26 and 27, it should be noted that in each configuration, rinse liquid is provided through inlet 470B and is extracted through the suction outlet 440B. The sole purpose of the arrangement illustrated in FIG. 24 is to purge fluid from the channel dead ends and the external configuration of the filter cartridge 400 is identical. For that reason, the process flow diagram illustrated in FIG. 26A, discussed with respect to FIG. 27, applies equally to the filter configuration found in FIG. 27 and a separate process flow diagram is not included herewith.

Particles are now deposited upon the top surface of filter element 425B in a configuration similar to that illustrated in FIGS. 17A-17B of the previous embodiment.

Figure 28:
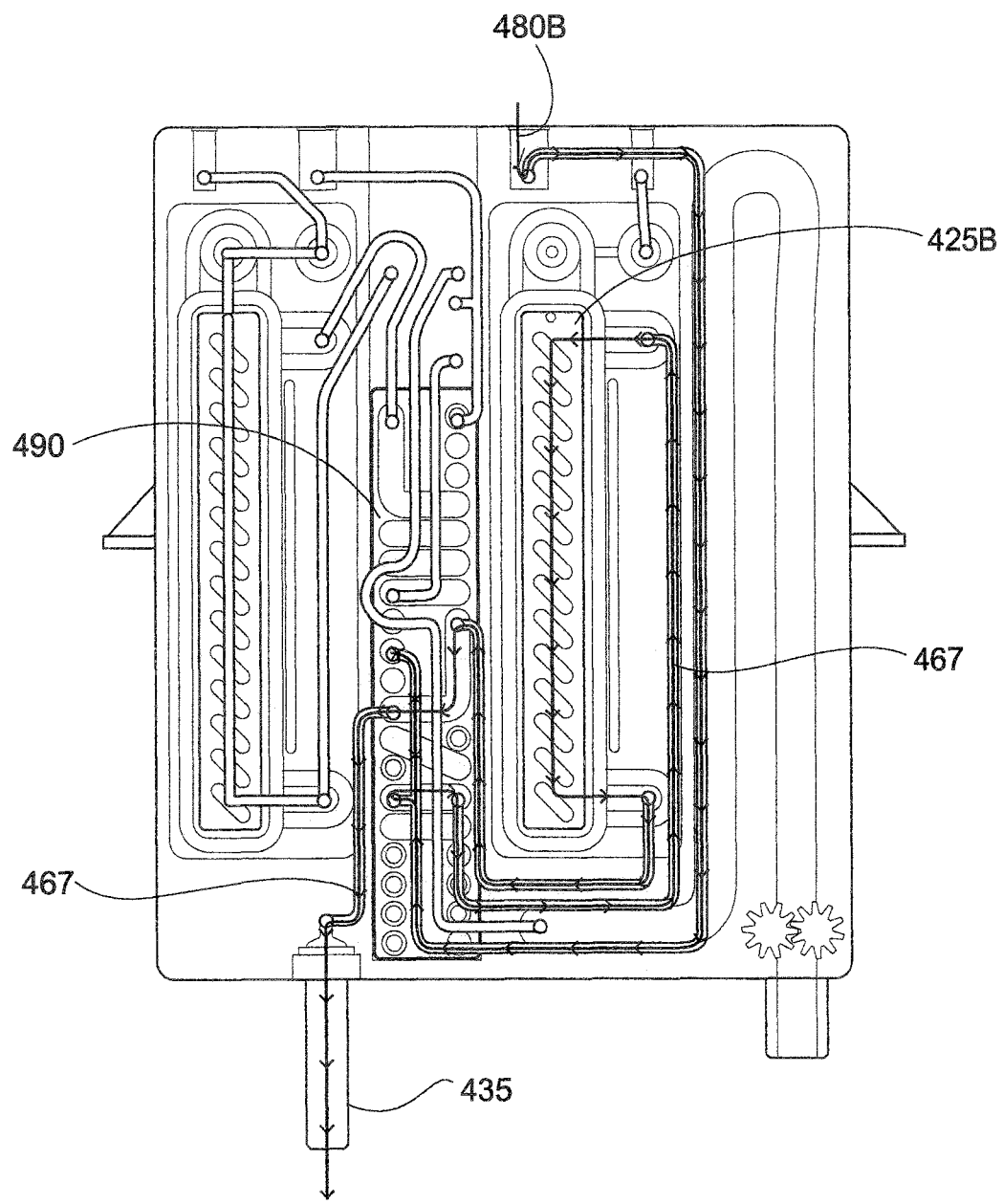

As illustrated in FIG. 28, at this time, foam is introduced at the foam inlet 480B and travels in the direction indicated by arrow 467 over the face of the filter element 425B to displace particles from the face of the filter element such that the filtered particles exit from the outlet 435. This arrangement is similar to that illustrated in FIGS. 17A-17B of the previous embodiment.

Figure 28A:
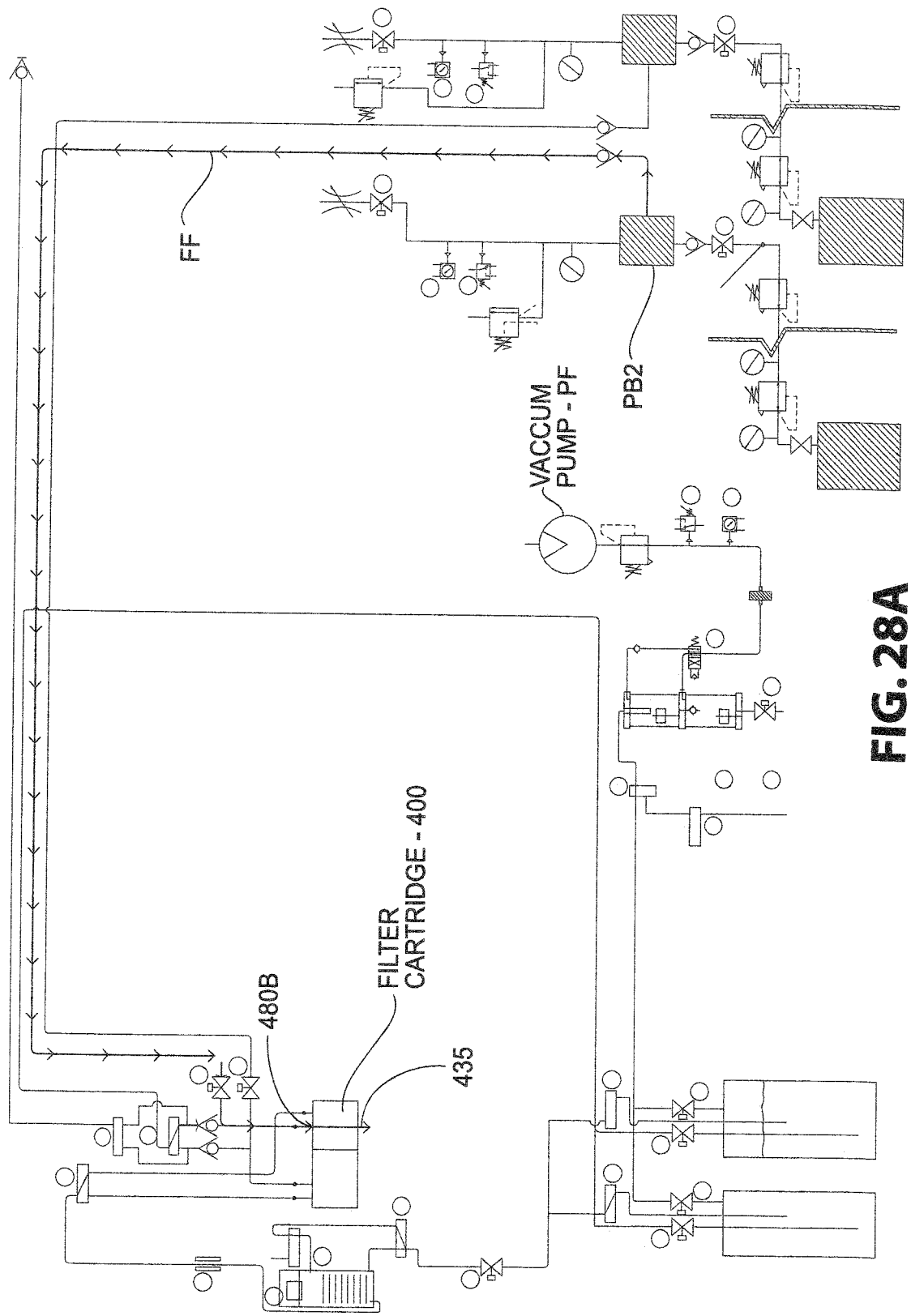

FIG. 28A shows the process flow for the arrangement just described with respect to FIG. 28. In particular, foam is provided by pressure vessel PB2 through lines FF to the inlet 480B of the filter cartridge 400 where the particles are removed from the face of the filter element 425B and discharged at the outlet 435 to provide a high concentration of particles suspended in a relatively low volume of liquid for subsequent analysis.

When utilized in a system, a multiplicity of filter arrangements 400 exist and the slider valve 490 for multiple filter arrangements 400 are activated such that a number of separate operations may be performed simultaneously. In particular, a filter arrangement, also known as a concentrator will be used on a processor including a cylindrical carousel. Additionally the filter arrangement 400, as illustrated, has alignment holes, and pins are utilized in these alignment holes.

It should be noted that the filter elements 425A, 425B are comprised of porous hydrophilic surfaces to permit liquid to pass therethrough but to restrict particles of a certain size. However, a portion of the filter elements 425A, 425B must be hydrophobic to permit passage of accumulated gasses generated during the filtering process. In particular, the foam utilized during the process creates gas that must be released to avoid restricting fluid flow. Also, a porous mesh, or screen, or damper 500 is provided adjacent to outlet 435 in the discharge flow path 502 to slow the exiting velocity of the concentrated solution from the filter arrangement.

Figure 29:
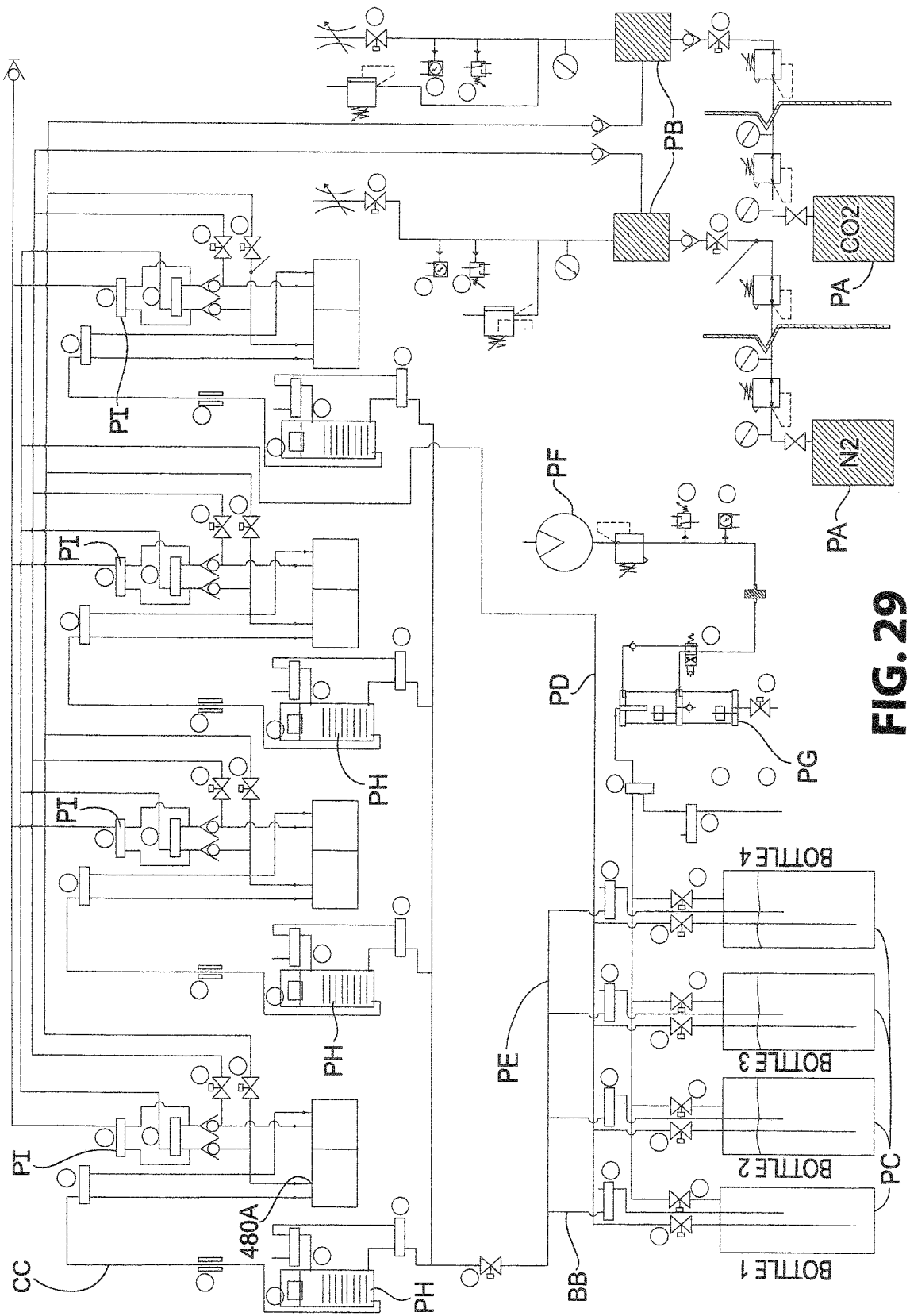
FIG. 29 is a process flow diagram showing a system utilizing four separate filter cartridges.

Directing attention to FIG. 29, it should be appreciated that bottles 2, 3, and 4 have liquid therein while bottle 1 is empty. In the past, a single container would have been sized to receive the liquid from all of the bottles resulting in a significantly larger container. The inventors have realized that by utilizing a single empty bottle with a volume sufficient to accept the liquid from another single bottle, it is possible to toggle the valving system such that there is always a single empty bottle into which the waste fluid may be directed after usage. In this manner, rather than have a single container to accept the volume of three bottles, it is possible to have a single container to accept the volume of one bottle so long as that container may alternate among the bottles.

Additionally, the flow meter PH is actually a mass meter used to measure the amount of volume that travels through the cassette. In the past, a peristaltic pump was used to fill an intermediate container with a known amount of rinse fluid and then the vacuum was used to pull that liquid through the filter. However, the inventors determined that it was more efficient to use only the vacuum to move fluid. While flow meters are available, the flow rate through the filter element depended upon the amount of clogging of the filter element so that the range of flows is great. Flow meters capable of measuring the flow are expensive and, therefore, another way to determine flow rate was needed. The mass meter used herein accumulates fluid that travels through the cartridge and evaluates the quantity of fluid entirely by weight. Once a specific weight representing a certain volume of fluid has been reached, the rinsing cycle stops. By measuring the weight of the fluid, utilizing a relatively simple scale, sufficiently accurate results are obtained without the need to use more sophisticated flow meters which are significantly more expensive and complex and at times have difficulty measuring the flow of the foam fluid. Therefore, the inventors have discovered a simple and elegant solution to determine the volume of flow over the filters using a simple technique based upon the weight of the cumulative fluid traveling therethrough.

While the arrangement described in FIG. 29 has been described with respect to cartridges using slider valves, such an arrangement is applicable to the different other cartridges and filters described herein as well as other similar cartridges and filters used for tangential filtering.

Figure 30:
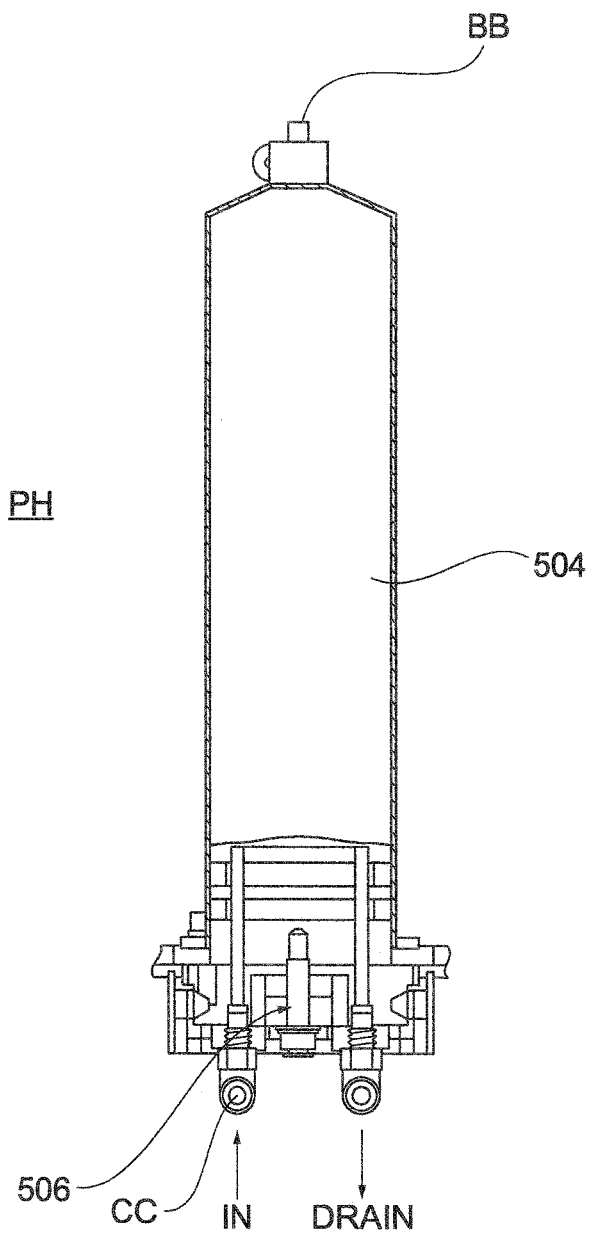
FIG. 30 is a partial cross-section side view of a mass meter illustrated schematically in FIG. 2.

FIG. 30 shows details of one such mass meter PH. In particular, the mass meter PH includes a canister 504, associated with a filter, which rests upon a load cell 506, such as a piezoelectric transducer. The weight of fluid within the canister 504 may be determined using this load cell 506. In such a fashion, an accurate estimation of the volume of fluid travelling through each filter is provided by the weight of the fluid within the canister 504 associated with that filter without the need to use direct volume measuring devices. As previously discussed, such direct volume measuring devices are not ideal for variable flow, such as that through a filter which may be partially clogged, and are relatively expensive.

Figure 31:
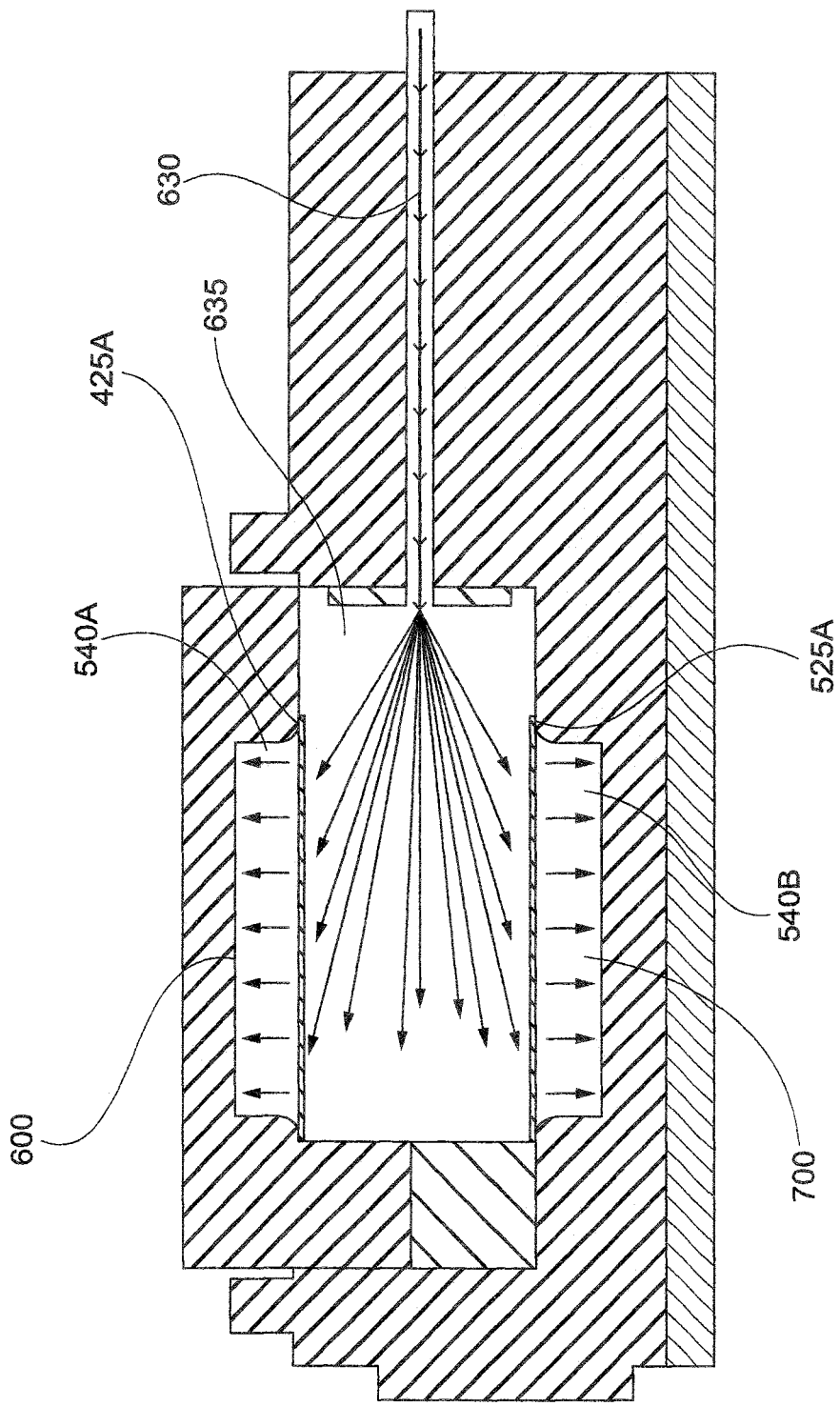
FIG. 31 is a schematic section view along arrows 29, in FIG. 22

Just as the dual filtering arrangement illustrated in FIGS. 18A and 18B are configured so that the filter element 315 and the filter element 320 provide twice the membrane surface within the same channel volume, so too is the configuration illustrated in FIG. 31.

Directing attention to FIG. 31, a top element 600 includes the filter element 425A while a bottom element 700 includes a filter element 525A. A fluid particle inlet 630 is in fluid communication with a chamber 635 common to both the filter element 425A and the filter element 525A. Suction passageways 540A, 540B are located on opposing sides of the filter elements 425A, 525A to provide a vacuum to filter the particles contained within the fluid particle solution introduced at the fluid particle inlet 630. In such a fashion, the filter element 425A and the filter element 525A provide twice the membrane surface with the same channel volume.

While what has been discussed so far is a rinse stage that rinses the particles with a rinse solution before the particles are wiped from the surface of the filter, the Applicant has also realized that in lieu of or in conjunction with the rinse stage, with the same cartridge configuration, the particles retained in the filter may be introduced through the same rinse inlet and the particles may then be irrigated with a stain suitable for Gram staining, such as crystal violet. Thereafter, the stained particles may be further rinsed or wiped from the filter for further processing. By introducing the stain suitable for Gram staining to the particles through the filter cartridge, not only is an external step eliminated, but time is saved.

While what has been discussed so far is the processing of a sample to extract particles such as bacteria or other microorganisms, it is still necessary to identify these particles.

The next portion of this disclosure is directed to a method for detecting, quantifying, gram type identification and micro-organisms presumptive identification, e.g., bacteria in urine samples. More particularly, the invention relates to a combination of the unique sample processing method, technology and system, hereinafter described, followed by microscopy image analysis which is fully automated to efficiently detect, quantify, and perform gram type identification performed on micro-organisms or other cells, in urine samples or other body fluids.

In general, current-day practice for identifying microorganisms, e.g., bacteria in urine samples involves a complex, lengthy, and expensive process for identifying and specifying micro-organisms in microbiology labs. In this current process, the samples are accepted into the lab. These specimens are then sorted and labeled and then they are inoculated onto blood agar medium using a sterilized loop. These three steps for preparing the samples for analysis are manually done wherein each urine sample is swabbed onto the blood agar medium in a covered culture disk or plate. If there are 50 to 100 samples, each sample has to be individually prepared, requiring much time and energy.

The specimens are then inserted into a dedicated incubator for a 24-hour period. A day later, the lab technicians screen the specimens for positive and negative cultures. In general, most of the cultures are negative and are manually reported. The organisms for the positive cultures are isolated and suspended in a biochemical fluid. This involves suspension, dilution, vortexing and turbidity measurements resulting in biochemical waste products. Again, this process for preparing the urine samples for analysis is done manually by lab technicians and again requiring much time and energy, particularly if there are 50 to 100 urine specimens that need to be analyzed.

The positive cultures are then subjected to a species identification and antibiotics susceptibility testing exposing the suspensions to multiple reagents. After another 6 to 24 hour incubation period, the findings are interpreted and reported by lab technicians. This entire process generally takes 11 steps and 50 hours to obtain specimen results and the process is labor intensive.

There is a need, therefore, particularly for rapid detection, quantification, gram type identification and presumptive species identification of the above lab procedure to provide a more efficient, but less time consuming process which requires less labor.

The subject invention as disclosed herein meets this need. The sample preparation system so far described concentrates and purifies the particles of a specimen based on dead end filtration and wet foam extraction. This process can be performed in about 10 minutes. However, now the particles must be identified.

Figure 32:
FIG. 32 is a process diagram generally illustrating the processing of and the identification of cells within a sample.
Figure 33A:
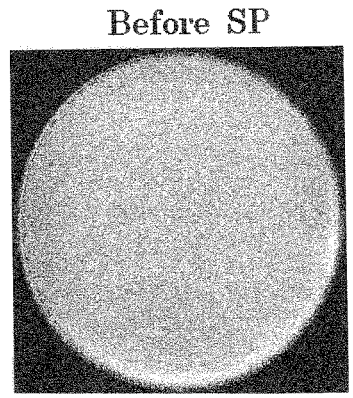
FIG. 33A illustrates bacteria from a urine specimen plated on blood agar using the WASP system without the concentrating process described herein.
Figure 33B:
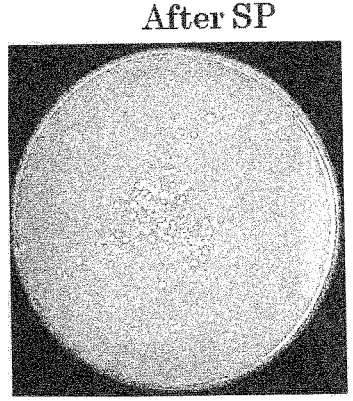
FIG. 33B illustrates bacteria from the same urine specimen plated on blood agar using the WASP system but using the concentrating process described herein.
Figure 33C:
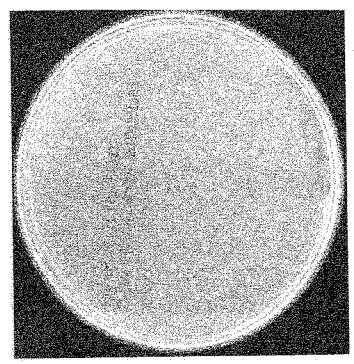
FIG. 33C illustrates bacteria from a urine specimen plated on Chromagar using the WASP system without the concentrating process described herein.
Figure 33D:
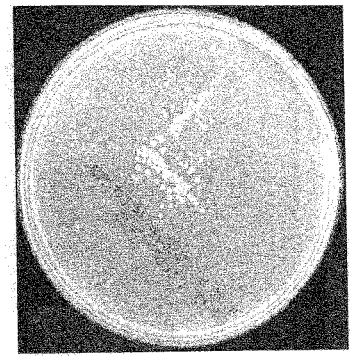
FIG. 33D illustrates bacteria from the same urine specimen plated on Chromagar using the WASP system but using the concentrating process described herein.
Figure 34:
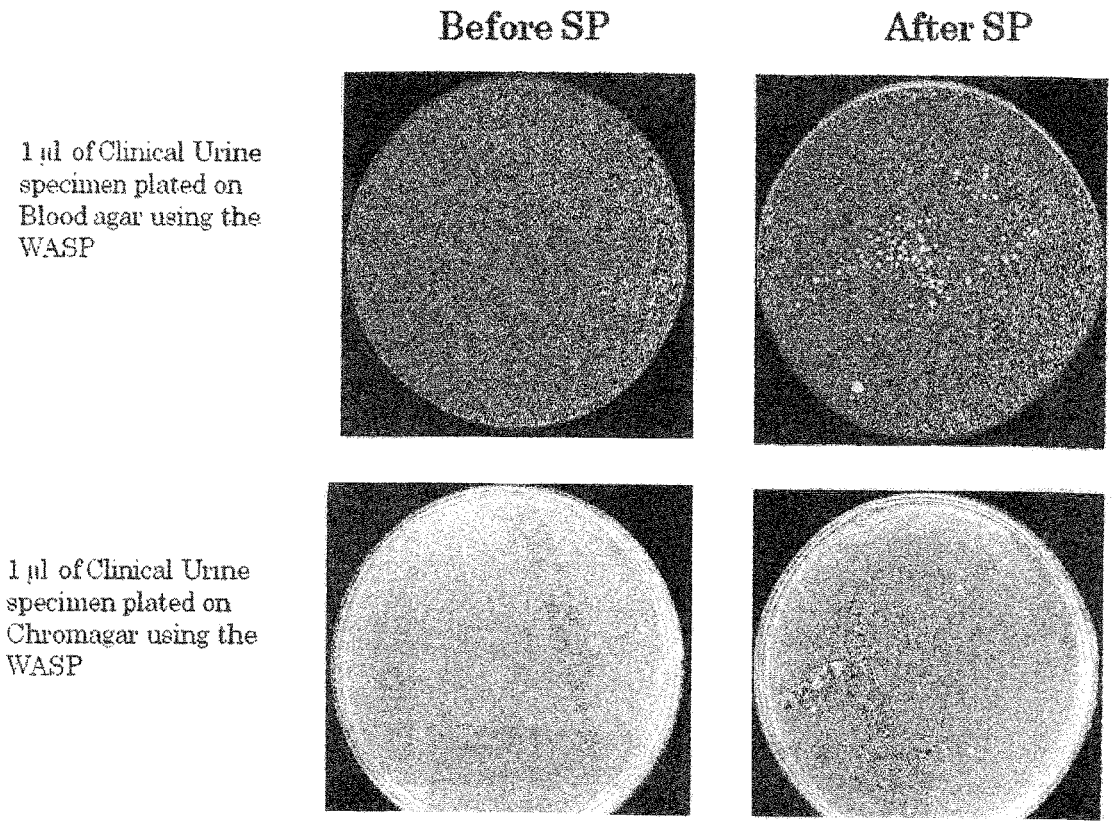
FIG. 34 illustrates two separate sets of a urine specimen, one set plated on blood agar and another set plated on Chromagar before and after processing, each using the WASP system.
Figure 35:
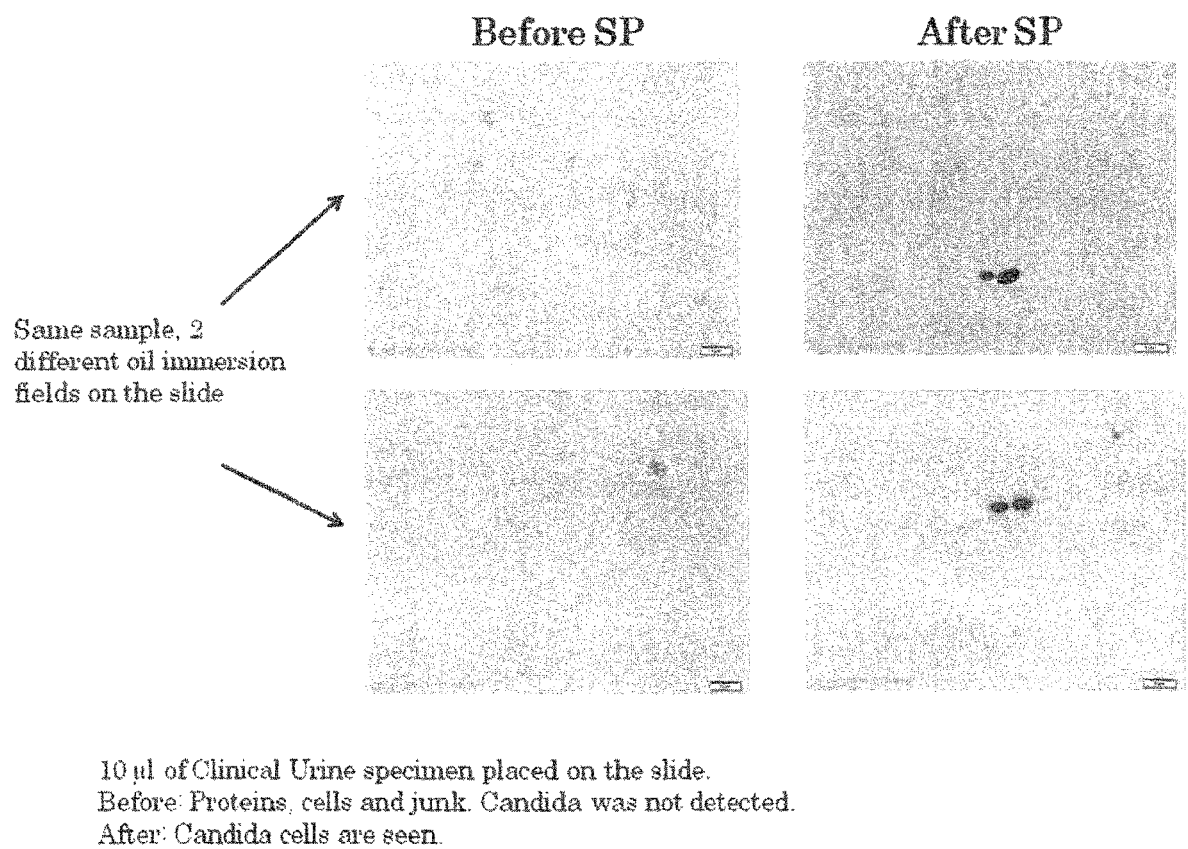
FIG. 35 is an image of two sets of a clinical urine specimen on slides before and after the concentrating process showing the effectiveness of the process in removing proteins, cells and material not of interest.
Figure 36:
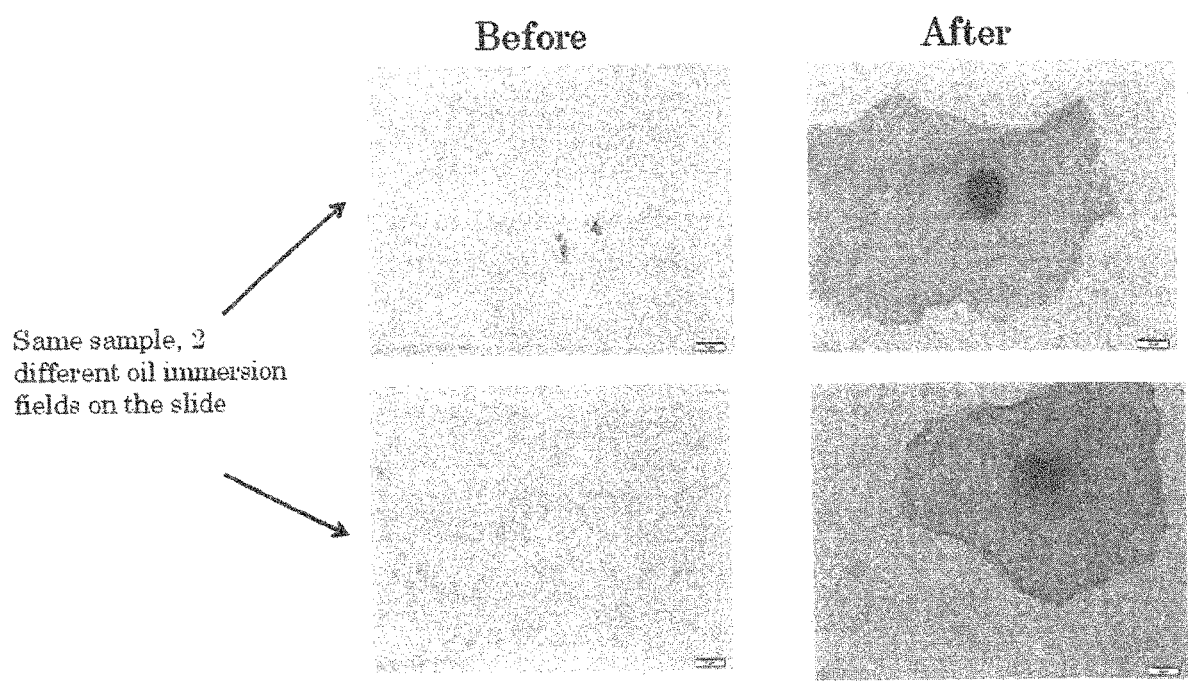
FIG. 36 is an image of two sets of CU specimens on slides before and after the concentrating process showing the effectiveness of the process in removing proteins, cells and material not of interest.
Figure 37:
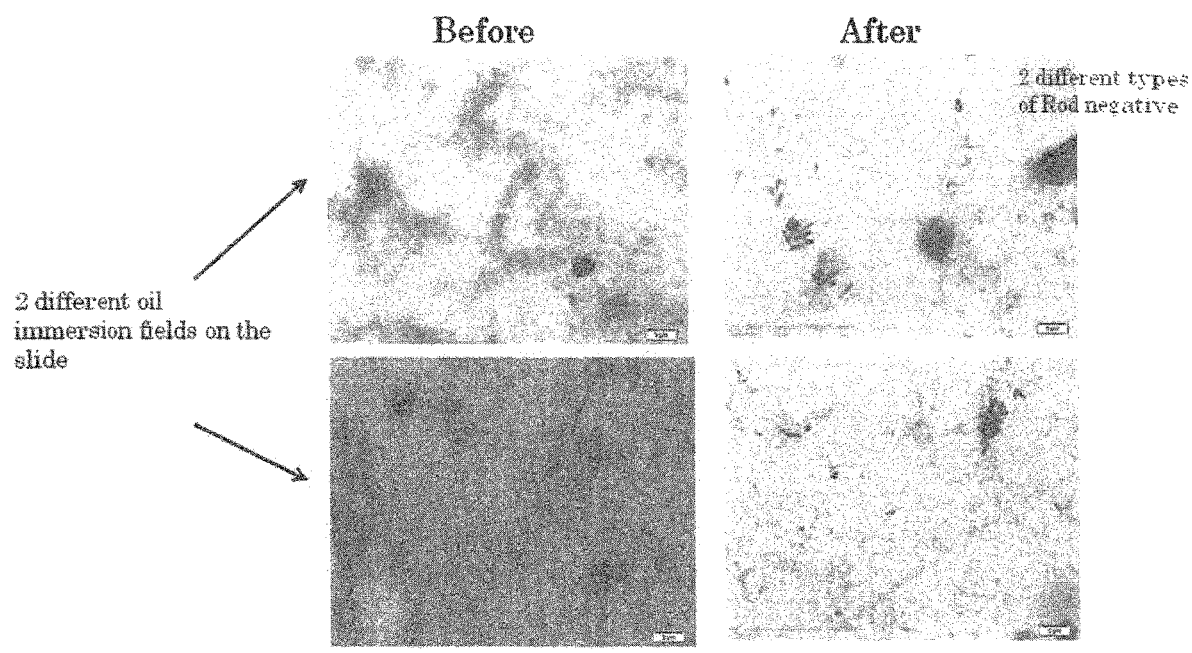
FIG. 37 is an image of two sets of CU specimens on slides before and after the concentrating process showing the effectiveness of the process in removing proteins, cells and material not of interest.

This process is illustrated in FIG. 32 beginning with a sample which is then processed in accordance with the previously described details of the invention. Thereafter, the particles of the concentrated sample are subjected to gram staining with subsequent scanning through a microscope and thereafter image analysis. As a part of the gram staining process, the particles may be smeared upon a medium that is suitable for use with a scanning microscope. While such steps for processing the concentrated sample may be performed manually, they may also be performed using a specimen processor such as the Copan WASP® Walkaway Specimen Processor which is an instrument for liquid sample processing for microbiology. The system provides gram slide preparation which thereafter is suitable for a scanning microscope and a subsequent image analysis.

FIGS. 33-37 show the effectiveness of concentrating particles using the sample processing method described herein. As an example, FIG. 33A shows an untreated clinical urine specimen on blood agar after a culturing period. No bacteria is easily visible. On the other hand, FIG. 33B shows a treated clinical urine specimen in which the bacteria particle have been concentrated using the system described herein. After a culturing period on the same blood agar, colonies of bacteria are easily visible. This same observation holds true for the specimens found in FIGS. 33C and 33D.

It is important to note that FIGS. 33A-33D are used only as an example of the effectiveness of the process to concentrate and purify a sample. The subject invention does not require culturing to identify organisms and, as a result, the time required to concentrating organisms for further analysis is substantially reduced.

FIGS. 34-37 are additional examples of the effectiveness of sample concentration in accordance with the subject invention.

Overall, the sample processor of the subject invention enables lower micro organisms concentration levels detection (e.g. 1 E4 CFU/ml for urine tract infection) and streamlines the current practice for analyzing urine samples. In addition to being fully automated, the sample processor is compact and self-contained. The sample processor does not require a sophisticated operator and rapidly processes the urine samples or specimens for the analysis. The suggested method increases efficiency, improves workload, saves time and money, and is easy to operate. The analysis can be performed in about ten minutes.

As a result, the sample processor output is a concentrated and purified version of the input fluid. Small particles and soluble material are removed from the sample while the amount of desired particles per fixed volume is increased. The purification aspect of the sample processor allows better staining by removing materials that interfere with the staining reagents. The purification aspect also removes clutter from the stained slide by removing small particles. The concentration aspect of the sample processor allows better detection since the field of view of the microscope sees only a limited volume of liquid placed on the side, so in low concentration, there may not be any elements of interest in many fields of view.

As a result, what has been described is a method for analyzing microbiological samples including a sample preparation unit followed by gram staining and smearing procedures (manual/automated) and analyzed by microscopy image analysis for detection (screening), quantification, gram type classification, and presumptive microorganism identification.

While specific embodiments of the invention have been described in detail, it will be appreciated by those skilled in the art that various modifications and alternatives to those details could be developed in light of the overall teachings of the disclosure. The presently preferred embodiments described herein are meant to be illustrative only and not limiting as to the scope of the invention which is to be given the full breadth of the appended claims and any and all equivalents thereof.

While specific embodiments of the invention have been described in detail, it will be appreciated by those skilled in the art that various modifications and alternatives to those details could be developed in light of the overall teachings of the disclosure. The presently preferred embodiments described herein are meant to be illustrative only and not limiting as to the scope of the invention which is to be given the full breadth of the appended claims and any and all equivalents thereof.

The invention claimed is:

1. Using a fluid/particle mixture and a filter element that captures over-sized particles and allows undersized particles to pass through, a method for separating and staining the over-sized particles from a fluid/particle mixture comprising the steps of:
   a) filtering the fluid/particle mixture through the filter element so that the over-sized particles are deposited on an upper surface of the filter element;
   b) irrigating the deposited particles retained by the filter element with a primary stain;
   c) tangentially wiping the upper surface of the filter element with an elution fluid to displace the deposited particles into a collector for further processing.

2. The method according to claim 1, wherein the primary stain is crystal violet suitable for Gram staining.

3. The method according to claim 1, further including, after the step of filtering the fluid/particle mixture, a step of rinsing undersized particles through the filter element with a rinse solution.

4. The method according to claim 1, wherein filtering the fluid/particle mixture through the filter element is done using suction through the filter element.

5. The method according to claim 1, wherein the over-sized particles are bacteria.

6. The method according to claim 1, wherein the filter element is a polycarbonate-type filter element which is a surface filter.

7. The method according to claim 1, wherein the filter element has pores with openings between approximately 0.01 microns and 50 microns wide.

8. The method according to claim 7, wherein the filter element has pores with openings approximately 0.4 microns wide.

9. The method according to claim 1, wherein the elution fluid is effervescent.

10. The method according to claim 1, wherein the elution fluid contains a foaming agent.

\* \* \* \* \*